(12) United States Patent
Jiang et al.

(10) Patent No.: US 6,774,220 B1
(45) Date of Patent: Aug. 10, 2004

(54) COMPOUNDS HAVING LECTINIC PROPERTIES AND THEIR BIOLOGICAL APPLICATIONS

(75) Inventors: Pan Hong Jiang, Beijing (CN); Aboubacar Kaba, Noisy Le Grand (FR); Francoise Chany-Fournier, Paris (FR); Italina Cerutti, La Varenne Saint Hilaire (FR); Charles Chany, Paris (FR)

(73) Assignee: Association pour le Développement de la Biothérapie Expérimentale et Appliquée, Paris (FR)

( * ) Notice: Subject to any disclaimer, the term of this patent is extended or adjusted under 35 U.S.C. 154(b) by 0 days.

(21) Appl. No.: 09/077,606

(22) PCT Filed: Dec. 4, 1996

(86) PCT No.: PCT/FR96/01937

§ 371 (c)(1),
(2), (4) Date: Jul. 30, 1998

(87) PCT Pub. No.: WO97/20927

PCT Pub. Date: Jun. 12, 1997

(30) Foreign Application Priority Data

Dec. 5, 1995 (FR) .......................................... 95 14336

(51) Int. Cl.[7] .................................................. C07K 1/00
(52) U.S. Cl. ....................... 530/396; 530/357; 530/412; 514/8; 514/12; 514/21; 424/185.1
(58) Field of Search ................................ 530/396, 412, 530/416, 357, 362, 364; 514/8, 12, 21

(56) References Cited

FOREIGN PATENT DOCUMENTS

| EP | 0 337 799 | 10/1989 |
|---|---|---|
| EP | 0 399 464 | 11/1990 |
| WO | 89/00581 | 1/1989 |

OTHER PUBLICATIONS

Current Protocols in Immunology. vol. 1, Wiley & Sons. pp. 2.4.1–2.4.2, 1991.*
Current Protocols in Molecular Biology pp. 11.41–11.45 Ausubel et al. Editors, Green Pub. Assn. & Wiley Interscience 1992.*
Lerner, Nature vol. 299 pp. 512–516, 1982.*
Zeng, F–Y, et al., Biol. Chem. Hoppe–Seyler, 375(6):393–399, 1994.*
Glass, C, et al. J. Cell Blol. 101:2366–2373, 1985.*
Glass, C and Fuchs, E. J. Cell Biol. 107:1337–1350, 1988.*
Kaba et al., 1993, Identification, isolation, and cloning of an endogenous interferon antagonist: sarcolectin. J. Interferon Research 13:S39, Abstract only.
Jiang et al., 1983, Sarcolectin: an interferon antagonist extracted from hamster sarcomas and normal muscles. J. Biol. Chem. 258:12361–12367.
Glass, 1988, Data Swiss Prot, see sequence alignment with SEQ ID NO:6, Accession No. P08729.
Glass, 1990, Data PIR2, see sequence alignment with SEQ ID NO:5., Accession No. S05602.
Jiang et al., 1999, Sarcolectin: complete purification for molecular cloning. Biochimie 81:701–707.
Kaba et al., 1999, Sarcolectin (SCL): structure and expression of the recombinant molecule. Biochimie 81:709–715.
Wellens et al., "A Silencer Element Which Specifically Interacts With NF–$_k$ B Sequences Contributes To The Regulation Of IFN–β, IL–2–Receptor and HIV–1 Promoters", vol. 13, pp. (1993).
Jiang et al., "Cell Distribution And antigenic Properties Of Mammalian Sarcolectins", *European Journal Of Cell Biology*, vol. 43:384–393, (1987).
Jiang et al., "Detection Of An Interferon Antagonist, Sarcolectin, In Human Sarcomas And Muscles", *Int. J. Cancer*, vol. 34:625–632, (1984).
Chany–Fournier et al., "Sarcolectin and Interferon In The Regulation Of Cell Growth", *Journal Of Cellular Physiology*, vol. 145:173–180, (1990).
Chany–Fournier et al., "Purification, Assay, and Characterization Of the Interferon Antagonist: Sarcolectin", *Method In Enzymology*, vol. 119:694–702, (1986).
Chany–Fournier et al., "Role Of Sarcolectins In The Regulation Of The Biological Functions Of Interferon", *The Interferon System*, vol. 24:189–194, (1985).
Zeng et al., "Migration Inhibitory Factor–Binding Sarcolectin From Human Placenta Is Indistinguishable From A Subfraction Of Human Serum Albumin", *Biol. Chem. Hoppe–Seyler*, vol. 375:393–399, (1994).
Subfraction Of Human Serum Albumin, *Biol. Chem. Hoppe-Seyler*, vol. 375:393–399, (1994).
Hillier, "Keratin Type II Cytoskeletal 7 (Human)", see sequence alignment with seq. ID. Nr 6 of invention, (1995), Gen Bank Accession No. H87337.
Glass et al., "Isolation, Sequence, And Differential Expression Of A Human K7 Gene In Simple Epithelial Cells", *The Journal of Cell Biology*, vol. 107(4):1337–1350.

* cited by examiner

Primary Examiner—Patrick J. Nolan
(74) Attorney, Agent, or Firm—Foley & Lardner, LLP

(57) ABSTRACT

The invention relates to nucleotide sequences capable of coding for polypeptides having lectinic properties and to corresponding polypeptides of the sarcolectin type and their uses in therapeutics. In particular, the invention relates to the use of polypeptides of the sarcolection type to stimulate immunity, if necessary in combination with interferon or butyroids. The use of specific inhibitors or antagonist peptides allows opposition to the constituent production of SCL. The antibodies directed against said peptides can be used in diagnostics and therapeutics.

46 Claims, 6 Drawing Sheets

SEQUENCE LISTING

<160> NUMBER OF SEQ ID NOS: 6

<210> SEQ ID NO 1
<211> LENGTH: 1831
<212> TYPE: DNA
<213> ORGANISM: Homo sapiens
<220> FEATURE:
<221> NAME/KEY: CDS
<222> LOCATION: (62)..(1468)

<400> SEQUENCE: 1

```
gaattccggc gagtgcgcgc tcctcctcgc ccgccgctag gtccatcccg gcccagccac      60 c atg tcc atc cac ttc agc tcc ccg gta ttc acc tcg cgc tca gcc gcc     109
  Met Ser Ile His Phe Ser Ser Pro Val Phe Thr Ser Arg Ser Ala Ala
   1               5                  10                  15 ttc tcg ggc cgc ggc gcc cag gtg cgc ctg agc tcc gct cgc ccc ggc        157
Phe Ser Gly Arg Gly Ala Gln Val Arg Leu Ser Ser Ala Arg Pro Gly
             20                  25                  30 ggc ctt ggc agc agc agc ctc tac ggc ctc ggc gcc tcg cgg ccg cgc        205
Gly Leu Gly Ser Ser Ser Leu Tyr Gly Leu Gly Ala Ser Arg Pro Arg
         35                  40                  45 gtg gcc gtg cgc tct gcc tat ggg ggc ccg gtg ggc gcc ggc atc cgc        253
Val Ala Val Arg Ser Ala Tyr Gly Gly Pro Val Gly Ala Gly Ile Arg
     50                  55                  60 gag gtc acc att aac cag agc ctg ctg gcc ccg ctg cgg ctg ggc gcc        301
Glu Val Thr Ile Asn Gln Ser Leu Leu Ala Pro Leu Arg Leu Gly Ala
 65                  70                  75                  80
```

-continued

| | |
|---|---|
| gac ccc ttc tcc cag cgg gtg cgc cag gag gag agc gag cag atc aag<br>Asp Pro Phe Ser Gln Arg Val Arg Gln Glu Glu Ser Glu Gln Ile Lys<br>                         85                                 90                          95 | 349 |
| acc ctc aac aac aag ttt gcc tcc ttc atc gac aag gtg cgg ttt ctg<br>Thr Leu Asn Asn Lys Phe Ala Ser Phe Ile Asp Lys Val Arg Phe Leu<br>                   100                            105                        110 | 397 |
| gag cag cag aac aag ctg ctg gag acc aag tgg acg ctg ctg cag gag<br>Glu Gln Gln Asn Lys Leu Leu Glu Thr Lys Trp Thr Leu Leu Gln Glu<br>                 115                          120                        125 | 445 |
| cag aag tcg gcc aag agc agc cgc ctc cca gac atc ttt gag gcc cag<br>Gln Lys Ser Ala Lys Ser Ser Arg Leu Pro Asp Ile Phe Glu Ala Gln<br>130                             135                        140 | 493 |
| att gct ggc ctt cgg ggt cag ctt gag gca atg cag gtg gat ggg ggc<br>Ile Ala Gly Leu Arg Gly Gln Leu Glu Ala Met Gln Val Asp Gly Gly<br>145                             150                        155                        160 | 541 |
| cgc ctg gag cag ggg ctg cgg acg atg cag gat gtg gtg gag gac ttc<br>Arg Leu Glu Gln Gly Leu Arg Thr Met Gln Asp Val Val Glu Asp Phe<br>                 165                          170                        175 | 589 |
| aag aat aag tac gaa gat gaa att aac cgc cgc aca gct gct gag aat<br>Lys Asn Lys Tyr Glu Asp Glu Ile Asn Arg Arg Thr Ala Ala Glu Asn<br>                 180                          185                        190 | 637 |
| gag ttt gtg gtc ctg aag aag gat gtg gat gct gcc tac atg agc aag<br>Glu Phe Val Val Leu Lys Lys Asp Val Asp Ala Ala Tyr Met Ser Lys<br>                 195                          200                        205 | 685 |
| gtg gag ctg gag gcc aag gtg gat gcc ctg aat gat gag atc aac ttc<br>Val Glu Leu Glu Ala Lys Val Asp Ala Leu Asn Asp Glu Ile Asn Phe<br>210                           215                        220 | 733 |
| ctc agg acc ctc aat gag acg gag ttg aca gag ctt cag tcc cag atc<br>Leu Arg Thr Leu Asn Glu Thr Glu Leu Thr Glu Leu Gln Ser Gln Ile<br>225                           230                        235                        240 | 781 |
| tcc gac aca tct gtg gtg ctg tcc atg gac aac agt cgc tcc ctg gac<br>Ser Asp Thr Ser Val Val Leu Ser Met Asp Asn Ser Arg Ser Leu Asp<br>                 245                          250                        255 | 829 |
| ctg gac ggc atc atc gct gag gtc aag gcg cag tat gag gag atg gcc<br>Leu Asp Gly Ile Ile Ala Glu Val Lys Ala Gln Tyr Glu Glu Met Ala<br>                 260                          265                        270 | 877 |
| aaa tgc agc cgg gct gag gct gaa gcc tgg tac cag acc aag ttt gag<br>Lys Cys Ser Arg Ala Glu Ala Glu Ala Trp Tyr Gln Thr Lys Phe Glu<br>                 275                          280                        285 | 925 |
| acc ctc cag gcc cag gct ggg aag cat ggg gac gac ctc cgg aat acc<br>Thr Leu Gln Ala Gln Ala Gly Lys His Gly Asp Asp Leu Arg Asn Thr<br>                 290                          295                        300 | 973 |
| cgg aat gag att tca gag atg aac cgg gcc atc cag agg ctg cag gct<br>Arg Asn Glu Ile Ser Glu Met Asn Arg Ala Ile Gln Arg Leu Gln Ala<br>305                           310                        315                        320 | 1021 |
| gag atc gac aac atc aag aac cag cgt gcc aag ttg gag gcc gcc att<br>Glu Ile Asp Asn Ile Lys Asn Gln Arg Ala Lys Leu Glu Ala Ala Ile<br>                 325                          330                        335 | 1069 |
| gcc gag gct gag gag cgt ggg gag ctg gcg ctc aag gat gct cgt gcc<br>Ala Glu Ala Glu Glu Arg Gly Glu Leu Ala Leu Lys Asp Ala Arg Ala<br>                 340                          345                        350 | 1117 |
| aag cag gag gag ctt gaa gcc gcc ctg cag cgg gcc aag cag gat atg<br>Lys Gln Glu Glu Leu Glu Ala Ala Leu Gln Arg Ala Lys Gln Asp Met<br>                 355                          360                        365 | 1165 |
| gca cgg cag ctg cgt gag tac cag gaa ctc atg agc gtg aag ctg gcc<br>Ala Arg Gln Leu Arg Glu Tyr Gln Glu Leu Met Ser Val Lys Leu Ala<br>370                           375                        380 | 1213 |
| ctg gac atc gag atc gcc acc tac cgc aag ctg ctg gag ggc gag gag<br>Leu Asp Ile Glu Ile Ala Thr Tyr Arg Lys Leu Leu Glu Gly Glu Glu | 1261 |

-continued

```
                385                 390                 395                 400
agc cgg ttg gct gga gat gga gtg gga gcc gcc aat atc tct gtg atg         1309
Ser Arg Leu Ala Gly Asp Gly Val Gly Ala Ala Asn Ile Ser Val Met
                405                 410                 415 aat tcc act ggt ggc agc agc agt ggc ggt ggc att ggg ctg acc ctc         1357
Asn Ser Thr Gly Gly Ser Ser Ser Gly Gly Gly Ile Gly Leu Thr Leu
            420                 425                 430 ggg gga acc atg ggc agc aat gcc ctg agc ttc tcc agc agt gcg ggt         1405
Gly Gly Thr Met Gly Ser Asn Ala Leu Ser Phe Ser Ser Ser Ala Gly
            435                 440                 445 cct ggg ctc ctg aag gct tat tcc atc cgg acc gca tcc gcc agt cgc         1453
Pro Gly Leu Leu Lys Ala Tyr Ser Ile Arg Thr Ala Ser Ala Ser Arg
        450                 455                 460 agg agt acc cgc gac tgagtcgcct cccaccactc cactcctcca gccaccaccc         1508
Arg Ser Thr Arg Asp
465 acaatcacag ccattgccga ggctgaggag tgtggggagc tggcgctcaa ggatgctcgt         1568 gccaagcagg aggagctgga agccgccctg cagcgggcca agcaggatat ggcacggcag         1628 ctgcgtgagt accaggaact catgagcgtg aagctggccc tggacatcga gatcgccacc         1688 taccgcaagc tgctggaggg cgaggagagc cggttggctg agatggagt gggagccgtg          1748 aatatctctg tgatgaattc cactggtggc agtagcagtg gcggtggcat tgggctagcc         1808 ctcgggggaa ccatgggcag caa                                                 1831

<210> SEQ ID NO 2
<211> LENGTH: 405
<212> TYPE: DNA
<213> ORGANISM: Homo sapiens
<220> FEATURE:
<221> NAME/KEY: CDS
<222> LOCATION: (1)..(405)

<400> SEQUENCE: 2 atg tcc atc cac ttc agc tcc ccg gta ttc acc tcg cgc tca gcc gcc          48
Met Ser Ile His Phe Ser Ser Pro Val Phe Thr Ser Arg Ser Ala Ala
 1               5                  10                  15 ttc tcg ggc cgc ggc gcc cag gtg cgc ctg agc tcc gct cgc ccc ggc          96
Phe Ser Gly Arg Gly Ala Gln Val Arg Leu Ser Ser Ala Arg Pro Gly
            20                  25                  30 ggc ctt ggc agc agc agc ctc tac ggc ctc ggc gcc tcg cgg ccg cgc         144
Gly Leu Gly Ser Ser Ser Leu Tyr Gly Leu Gly Ala Ser Arg Pro Arg
        35                  40                  45 gtg gcc gtg cgc tct gcc tat ggg ggc ccg gtg ggc gcc ggc atc cgc         192
Val Ala Val Arg Ser Ala Tyr Gly Gly Pro Val Gly Ala Gly Ile Arg
    50                  55                  60 gag gtc acc att aac cag agc ctg ctg gcc ccg ctg cgg ctg ggc gcc         240
Glu Val Thr Ile Asn Gln Ser Leu Leu Ala Pro Leu Arg Leu Gly Ala
65                  70                  75                  80 gac ccc ttc tcc cag cgg gtg cgc cag gag gag agc gag cag atc aag         288
Asp Pro Phe Ser Gln Arg Val Arg Gln Glu Glu Ser Glu Gln Ile Lys
                85                  90                  95 acc ctc aac aac aag ttt gcc tcc ttc atc gac aag gtg cgg ttt ctg         336
Thr Leu Asn Asn Lys Phe Ala Ser Phe Ile Asp Lys Val Arg Phe Leu
            100                 105                 110 gag cag cag aac aag ctg ctg gag acc aag tgg acg ctg ctg cag gag         384
Glu Gln Gln Asn Lys Leu Leu Glu Thr Lys Trp Thr Leu Leu Gln Glu
        115                 120                 125 cag aag tcg gcc aag agc agc                                             405
Gln Lys Ser Ala Lys Ser Ser
```

130                 135

<210> SEQ ID NO 3
<211> LENGTH: 469
<212> TYPE: PRT
<213> ORGANISM: Homo sapiens

<400> SEQUENCE: 3

Met Ser Ile His Phe Ser Ser Pro Val Phe Thr Ser Arg Ser Ala Ala
 1               5                  10                  15

Phe Ser Gly Arg Gly Ala Gln Val Arg Leu Ser Ser Ala Arg Pro Gly
             20                  25                  30

Gly Leu Gly Ser Ser Ser Leu Tyr Gly Leu Gly Ala Ser Arg Pro Arg
         35                  40                  45

Val Ala Val Arg Ser Ala Tyr Gly Gly Pro Val Gly Ala Gly Ile Arg
 50                  55                  60

Glu Val Thr Ile Asn Gln Ser Leu Leu Ala Pro Leu Arg Leu Gly Ala
 65                  70                  75                  80

Asp Pro Phe Ser Gln Arg Val Arg Gln Glu Glu Ser Glu Gln Ile Lys
                 85                  90                  95

Thr Leu Asn Asn Lys Phe Ala Ser Phe Ile Asp Lys Val Arg Phe Leu
            100                 105                 110

Glu Gln Gln Asn Lys Leu Leu Glu Thr Lys Trp Thr Leu Leu Gln Glu
        115                 120                 125

Gln Lys Ser Ala Lys Ser Ser Arg Leu Pro Asp Ile Phe Glu Ala Gln
    130                 135                 140

Ile Ala Gly Leu Arg Gly Gln Leu Glu Ala Met Gln Val Asp Gly Gly
145                 150                 155                 160

Arg Leu Glu Gln Gly Leu Arg Thr Met Gln Asp Val Val Glu Asp Phe
                165                 170                 175

Lys Asn Lys Tyr Glu Asp Glu Ile Asn Arg Arg Thr Ala Ala Glu Asn
            180                 185                 190

Glu Phe Val Val Leu Lys Lys Asp Val Asp Ala Ala Tyr Met Ser Lys
        195                 200                 205

Val Glu Leu Glu Ala Lys Val Asp Ala Leu Asn Asp Glu Ile Asn Phe
    210                 215                 220

Leu Arg Thr Leu Asn Glu Thr Glu Leu Thr Glu Leu Gln Ser Gln Ile
225                 230                 235                 240

Ser Asp Thr Ser Val Val Leu Ser Met Asp Asn Ser Arg Ser Leu Asp
                245                 250                 255

Leu Asp Gly Ile Ile Ala Glu Val Lys Ala Gln Tyr Glu Glu Met Ala
            260                 265                 270

Lys Cys Ser Arg Ala Glu Ala Glu Ala Trp Tyr Gln Thr Lys Phe Glu
        275                 280                 285

Thr Leu Gln Ala Gln Ala Gly Lys His Gly Asp Asp Leu Arg Asn Thr
    290                 295                 300

Arg Asn Glu Ile Ser Glu Met Asn Arg Ala Ile Gln Arg Leu Gln Ala
305                 310                 315                 320

Glu Ile Asp Asn Ile Lys Asn Gln Arg Ala Lys Leu Glu Ala Ala Ile
                325                 330                 335

Ala Glu Ala Glu Glu Arg Gly Glu Leu Ala Leu Lys Asp Ala Arg Ala
            340                 345                 350

Lys Gln Glu Glu Leu Glu Ala Ala Leu Gln Arg Ala Lys Gln Asp Met
        355                 360                 365

```
Ala Arg Gln Leu Arg Glu Tyr Gln Glu Leu Met Ser Val Lys Leu Ala
    370                 375                 380

Leu Asp Ile Glu Ile Ala Thr Tyr Arg Lys Leu Leu Glu Gly Glu Glu
385                 390                 395                 400

Ser Arg Leu Ala Gly Asp Gly Val Gly Ala Ala Asn Ile Ser Val Met
                405                 410                 415

Asn Ser Thr Gly Gly Ser Ser Gly Gly Gly Ile Gly Leu Thr Leu
            420                 425                 430

Gly Gly Thr Met Gly Ser Asn Ala Leu Ser Phe Ser Ser Ala Gly
            435                 440                 445

Pro Gly Leu Leu Lys Ala Tyr Ser Ile Arg Thr Ala Ser Ala Ser Arg
    450                 455                 460

Arg Ser Thr Arg Asp
465

<210> SEQ ID NO 4
<211> LENGTH: 135
<212> TYPE: PRT
<213> ORGANISM: Homo sapiens

<400> SEQUENCE: 4

Met Ser Ile His Phe Ser Ser Pro Val Phe Thr Ser Arg Ser Ala Ala
  1               5                  10                  15

Phe Ser Gly Arg Gly Ala Gln Val Arg Leu Ser Ser Ala Arg Pro Gly
                 20                  25                  30

Gly Leu Gly Ser Ser Ser Leu Tyr Gly Leu Gly Ala Ser Arg Pro Arg
            35                  40                  45

Val Ala Val Arg Ser Ala Tyr Gly Gly Pro Val Gly Ala Gly Ile Arg
     50                  55                  60

Glu Val Thr Ile Asn Gln Ser Leu Leu Ala Pro Leu Arg Leu Gly Ala
 65                  70                  75                  80

Asp Pro Phe Ser Gln Arg Val Arg Gln Glu Glu Ser Glu Gln Ile Lys
                 85                  90                  95

Thr Leu Asn Asn Lys Phe Ala Ser Phe Ile Asp Lys Val Arg Phe Leu
                100                 105                 110

Glu Gln Gln Asn Lys Leu Leu Glu Thr Lys Trp Thr Leu Leu Gln Glu
            115                 120                 125

Gln Lys Ser Ala Lys Ser Ser
    130                 135

<210> SEQ ID NO 5
<211> LENGTH: 15
<212> TYPE: PRT
<213> ORGANISM: Homo sapiens

<400> SEQUENCE: 5

Gly Leu Gly Ala Ser Arg Pro Arg Val Ala Val Arg Ser Ala Tyr
  1               5                  10                  15

<210> SEQ ID NO 6
<211> LENGTH: 15
<212> TYPE: PRT
<213> ORGANISM: Homo sapiens

<400> SEQUENCE: 6

Asp Pro Phe Ser Gln Arg Val Arg Gln Glu Glu Ser Glu Gln Ile
  1               5                  10                  15
```

COMPOUNDS HAVING LECTINIC PROPERTIES AND THEIR BIOLOGICAL APPLICATIONS

BACKGROUND OF THE INVENTION

1. Field of the Invention

The invention relates to compounds having lectinic properties, and to their biological applications.

More particularly, it relates to proteins or polypeptides of the sarcolectin type.

2. Description of the Related Art

It is known that this term has been used to designate the lectins identified in human osteogenic sarcomas or those induced in the hamster (after inoculation with Moloney sarcoma virus) where they are present in large quantities. However, sarcolectins are also found in a wide variety of normal or tumoral tissues in vertebrates. (primates, rodents, fowl).

They may also be detected on the surface of normal or transformed cells of human or animal origin.

Purified preparations of sarcolectins have already been described and their properties reported.

The most regularly characterised physical-chemical properties are:

sensitivity to proteases (trypsin, PRONASE® (proteolytic enzyme), but also resistance to controlled treatments, under certain conditions, with pepsin;

resistance to temperature variations (−20° C. to +100° C.);

resistance to pH variations (2 to 8);

resistance to detergents such as SDS and di-thiothreitol;

migration in SDS-PAGE gel of the protein in the molecular weight region of 65–55 kd.

Their biological properties are of three orders (see references (1) to (8) given at the end of the specification, with the other references mentioned below, in the document "Bibliographic references"):

agglutination of normal or transformed cells (activity at cell membrane level). Cytoagglutination may be inhibited due to the affinity of sarcolectins for simple sugars.

stimulation of the growth of human T and B lymphocytes, Daudi lymphoid cells, and cells adhering to the substrate such as L929 murine cells, transformed rat fibroblasts (Fr3T3) and human fibroblasts (FS4). Sarcolectins thus act as promoters of cell growth, of undetermined specificity;

reduction or suppression of the antiviral state preestablished by interferon (IFN) and restoration in the cell of the initial sensitivity to the virus. After antiviral resistance has been established, SCLs inhibit the continuation of the synthesis of interferon-dependent proteins, for example, protein kinase and 2–5A synthetase. Restoration of the initial state depends on the doses of SCL and may be more or less complete. When the cell is restored, it is possible either to stimulate growth by SCLs or by other growth factors, or on the other hand to re-treat the cells with IFN in order to develop antiviral resistance again.

SUMMARY OF THE INVENTION

A The invention is based on obtaining highly purified preparations of SCL which have made it possible to develop strategies leading to the isolationof cDNA clones coding for a 55 kd protein, the study of which has revealed unexpected biological properties.

It should be noted that all previous attempts prior to the invention retained the 65 kd protein as the molecule having the biological properties of SCL. During identifications based on electrophoresis on acrylamide gel followed by Western blot, the major band in the 65 kd region had in fact been retained as holding all the biological properties: the 55 kd band is not constantly observed and moreover appears minor in all cases. Now, in a surprising manner, it appears that the 65 kd band corresponds to an artifact which results from the fixation of a few SCL molecules on albumin, but that the molecule possessing sarcolectin-type properties is in reality the 55 kd protein which contains all the genetic information responsible for the biological expression of the molecule.

The object of the invention is, therefore, to provide various products binding to 55 kd SCL, namely in particular, proteins, polypeptides or fragments thereof, DNA sequences coding for these proteins or these polypeptides or fragments thereof, or on the other hand, inhibiting their expression, and antibodies directed against these proteins, polypeptides or fragments thereof.

The term sarcolectin or SCL, as used hereinafter in the specification, will designate without distinction proteins, polypeptides and fragments of these compounds, or their derivatives, as long as they possess lectinic properties as defined according to the invention.

The invention also relates to processes for obtaining these various products.

According to another aspect, the invention also relates to biological applications for these products.

The sequences of nucleotides according to the invention are sequences isolated from their natural environment and are characterised in that they contain at least part of the sequence SEQ ID NO: 1, one or more nucleotides being modified if necessary, it being understood that these sequences are capable of coding for sarcolectins, i.e. proteins, polypeptides or fragments of these compounds, or derivatives, having lectinic properties.

The sequence SEQ ID NO: 1 is given at the end of the specification, with the other sequences mentioned below, in the document entitled "List of sequences".

The term lectinic properties means the ability of the SCLs to agglutinate normal or transformed cells, their stimulating effect on cell growth and their effect of inhibiting the antiviral effect induced by interferon, under the conditions described in (8).

Such sequences used according to conventional recombinant DNA techniques are capable of coding for proteins or polypeptides, or fragments thereof, having lectinic activity, comprising at least one chain of amino acids as indicated in SEQ ID NO: 1, in which one or more amino acids are modified, if necessary.

These sequences are further characterised in that they are capable of hybridising with at least one fragment of SEQ ID NO: 1 carrying at least part of the genetic information for a sarcolectin. This hybridisation may be carried out under stringent conditions, but also under relaxed conditions as described in (10).

The invention relates in particular to the nucleotide sequence corresponding to the open reading frame running from position 62 to position 1429 in SEQ ID NO: 1.

In this sequence, the domains of the 5' ends and/or 3' ends are particularly preferred given that they contain the genetic information for the fragments possessing the said lectinic properties.

From this point of view, the sequence of about 405 bp running from position 62 to 467 in SEQ ID NO: 1, as represented in SEQ ID NO: 2, is quite particularly preferred.

These 5' and 3' domains are characterised in that they contain a large proportion of amino acids capable of being phosphorylated, such as serine, threonine and tyrosine.

The various sequences mentioned above may be genome sequences or of the genome type since certain chains of nucleotides may be separated by introns which will be excised to lead to the expression of mature SCLS.

The corresponding mRNA sequences, or the antisense sequences corresponding to the sequences defined above, and the complementary sequences of these various sequences, also come within the scope of the invention.

These various sequences of nucleotides are further characterised in that they contain no DNA of mammals, infectious agents, prions and other materials of natural products.

As indicated above, the invention also relates to the sequences derived from SEQ ID NO: 1.

These derived sequences are obtained by modification, substitution, alteration, mutation or genetic and/or chemical deletion of one or more nucleotides of SEQ ID NO: 1 or of a fragment of SEQ ID NO: 1, it being understood that they possess genetic information for coding for an SCL retaining at least in part the lectinic activity presented by the polypeptide coded by SEQ ID NO: 1, this activity being increased, if necessary.

If desired, these modifications make it possible to adapt the sequences defined above to the expression in a type of vector or host, or to facilitate cell penetration of the coded polypeptide or to increase its activity.

The invention also relates to the expression vectors containing at least one of the nucleotide sequences defined above, under the control of a suitable promoter. It relates in particular to the vectors containing all or part of SEQ ID NO: 1 or SEQ ID NO: 2, or their antisense sequences.

The host cells transfected by these vectors, which contain the recombinant proteins expressed, are also part of the invention.

The cells used for the transfections are, conventionally, eukaryotic or prokaryotic cells or vegetable cells.

The invention also relates to SCLs having lectinic properties as defined above, as novel chemicals.

The invention thus relates to proteins or polypeptides or to their fragments or their derivatives, characterised in that they possess lectinic activity and contain at least part of an amino acid chain in the sequence coded by one of the nucleotide sequences defined above, one or more amino acids being modified, if necessary, as long as this modification does not adversely affect the lectinic properties of the proteins, polypeptides or their fragments, or their derivatives.

These proteins contain no element capable of being confused with albumin.

The invention relates in particular to the SCLs having an amino acid chain in SEQ ID NO: 3 or in SEQ ID NO: 4.

The SCL corresponding to the open reading frame in the sequence SEQ ID NO: 1 contains 469 amino acids and has a molecular weight evaluated at 55 kd.

The sequences of the 5' and/or 3' regions of SEQ ID NO: 3, particularly those of the 5' region corresponding to SEQ ID NO: 4 are essentially responsible for the lectinic function of the SCLs defined above.

Other particularly preferred peptide sequences correspond to peptides having a structure corresponding to that of SEQ ID NO: 4, running from position 41 to 55 in SEQ ID NO: 1 or NO: 4.

It is the peptides having sequence SEQ ID NO: 5 or peptides derived from this sequence and characterized in that they are recognised by monoclonal antibodies capable of reacting with SEQ ID NO: 1, by their own antibodies, but in that they do not react with antibodies directed against the peptide fragment 81 to 95 in SEQ ID NO: 1.

Other preferred peptides sequences correspond to the peptides of SEQ ID NO: 6, having a structure corresponding to that of the sequence running from position 81 to 95 in SEQ ID NO: 1.

It is the peptides having sequence SEQ ID NO: 6 or peptides derived from this sequence, and characterized in that the antibodies directed against this fragment do not recognise the fragment 41–55 above.

It should be remembered that by peptide derivatives ismeant the sequences differing by one or more amino acids (in particular by modification, substitution, deletion) but recognised by the same antibodies as the native sequences.

The peptides SEQ ID NO: 5 and SEQ ID NO: 6, and their derivatives, are capable, when they are fixed on a susceptible cell in vitro, of inhibiting the fixation of the complete molecule and of hindering the expression of its functions, the effects being less pronounced with the peptide SEQ ID NO: 6 or its derivatives.

The SCLs of the invention are further characterised in that they are those obtained by expression, in an appropriate host according to recombinant DNA techniques, of an expression vector containing a DNA sequence of the kind defined above, recovery of the SCL expressed, and purification.

Other SCLs of the invention are fragments or derivatives obtained by modification of the sequences SEQ ID NO: 3 or SEQ ID NO: 4, as long as they retain at least in part the lectinic properties defined above.

As indicated in connection with the nucleotide sequences, the term modification means any mutation, deletion, substitution and/or addition of one or more amino acids, obtained directly at the level of the amino acid chain, or indirectly by modifying the coding nucleotide sequence.

Other SCLs are those obtained by purification from tissue extracts.

The invention relates in particular to the purified SCLs such as those obtained from tissue extracts, by operating as follows:

treatment of the tissue extract containing lectins with pepsin in a controlled manner or at an acid pH, under conditions that make it possible to remove at least the major part of the contaminating proteins, particularly albumin, whilst retaining the lectinic activity;

chromatography on SEPHACRYL® (agarose with acrylamide links, a gel filtration media with a fractionation range of 5,000–250,000 daltons for globular proteins) S-200 chromatography on an ion exchange resin such as DEAE-cellulose or CM-TRISACRYL® (agarose with acrylamide links, a gel filtration media with a fractionation range 200–2,500 daltons);

affinity chromatography using a sugar such as N-acetylneurminic acid as ligand, the purity of the SCLs being verified by reversed-phase HPLC.

The highly purified SCLs are characterised in that they appear to be practically wholly devoid of albumin. They give a single HPLC peak and, after chromatography on SDS gel and denaturation, show three characteristic bands formed from proteins with an estimated size of 65 kd, 55 kd and ≦14 kd.

The invention relates quite particularly to the SCL characterised by a molecular weight of about 55 kd, as estimated by SDS-PAGE by comparison with polypeptides of defined molecular weight.

It possesses structural and functional properties which distinguish it from the conventional group of intermediate filaments although it is recognised by a type 7 mesothelial anti-cytokeratin monoclonal antibody.

In fact, it takes the form of a monomer, possibly dimer, whilst intermediate filaments are generally polymerised to tetramers or higher polymers. It is an extracellular protein secreted in vivo and in vitro whilst intermediate filaments are intracellular or participate in maintaining the structure.

They possess lectinic properties, that is, they inhibit the actions of IFN, they have the capacity to stimulate cell synthesis and to agglutinate cells. These properties are essentially conferred by the 5' end, as borne out by digestion by pepsin which is able to suppress the function of stimulating the synthesis of DNA, with retention of the size and sedimentation in SDS-PAGE.

By providing a highly purified SCL, the invention makes it possible on the one hand to characterise the molecule and on the other hand to obtain sufficiently pure antibodies to characterise the antigen structure of the SCLs.

The invention also relates to processes for obtaining nucleotide sequences and the SCLs defined above.

In order to obtain the nucleotide sequences, it is possible to operate by means of synthesis according to conventional techniques. As a variant, particularly for obtaining at least a part of the sequences of the SEQ ID NO: 1 or SEQ ID NO: 2 type, a bank of cDNA is screened with the aid of specific probes such as antibodies directed against the purified 55 kd protein mentioned above and described in more detail in the examples, or mRNA. The sequences of interest are isolated, if necessary modified as desired, according to the applications envisaged, and undergo one or more purification treatments.

In order to obtain the SCLs of the invention, these sequences are advantageously introduced into an appropriate expression vector, under the control of a promoter, for the purpose of transfection of a host cell.

By applying the conditions required to obtain the expression of the SCL of interest with lectinic activity, the latter is synthesised and, after lysis of the cells or simply after secretion, it is recovered in the recombinant form and undergoes at least one purification stage.

For the production of SCLs, prokaryote systems such as bacteria will be used, or eukaryotes such as insect cells (Baculovirus system), or yeasts, advantageously those available commercially. It is also possible to use animal cells such as CHO hamster cells, or primate cells transfected with the appropriate gene.

The SCLs of the invention may also be obtained by synthesis.

The processes described above allow the purification of the SCL molecules whilst retaining their biological properties.

The invention relates in particular to a process for obtaining SCL with a high degree of purity from tissue extracts, characterised in that it comprises stages for treating the tissue extract containing lectins with pepsin in a controlled manner or at an acid pH, followed by chromatography under conditions whereby at least the majority of the contaminating proteins, quite particularly albumin, can be removed whilst retaining the lectinic activity.

These chromatography stages comprise:
running the pre-treated tissue extract through SEPHACRYL® (agarose with acrylamide links, a gel filtration media with a fractionation range of 5,000–250,000 daltons for globular proteins) S-200;

recovering the fraction containing most of the lectinic activity as measured by the cell agglutination test;
running this fraction through ion exchange resins, particularly DEAE-cellulose and CM-TRISACRYL® (agarose with acrylamide links, a gel filtration media with a fractionation range of 200–2,500 daltons);
running the fraction containing most of the lectinic activity through a column containing a sugar such as N-acetylneuraminic acid as ligand.

This succession of stages provides a technical solution to the problem of separating the contaminating albumin and makes it possible to remove it in spite of the size, which is similar to that of SCL, certain physical-chemical properties which are similar to those of SCL, and possible interactions between albumin and SCL.

The tissue extract treatment stage is carried out with the aid of pepsin, operating under controlled conditions. The respective concentrations are of the order of 4 to 8%, preferably about 6% for the tissue extract, and 0.5 to 2 mg/ml, preferably about 1 mg/ml for a pepsin having an activity of the order of 2500 to 2700 units/mg.

Tissue extract treatment conditions which have proved to be advantageous involve incubation of the reaction mixture at about 37° C., pH 2, for about 1 h 30 to 2 h 30, in particular for 2 hours.

The enzyme activity is then stopped by raising the pH to a value close to neutrality.

The extract thus treated undergoes a succession of chromatographic stages.

1—Chromatography on SEPHACRYL® (agarose with acrylamide links, a gel filtration media with a fractionation range of 5,000–250,000 daltons for globular proteins)

Preferably, this extract is centrifuged beforehand and the supernatant undergoes filtration over a SEPHACRYL® (agarose with acrylamide links, a gel filtration media with a fractionation range of 5,000–250,000 daltons for globular proteins) S-200 gel. The active fractions are recovered by elution with a buffer solution such as PBS in a quantity of 15 to 25 ml/h.

2—Chromatography on DEAE-cellulose The fractions recovered are pooled and the fractions with the maximum lectinic activity undergo chromatography on DEAE-cellulose which as been swollen beforehand and equilibrated with a buffer solution with a pH around neutrality, particularly a pH of the order of 7.6.

Elution is carried out with the buffer solution to which has been added a salt with a molarity ranging from 0 to 0.5 M representing a linear gradient of pH 7.6 to 4.0. A satisfactory rate of elution is of the order of 20 ml/h.

3—Chromatogra on CM-TRISACRYL® (agarose with acrylamide links, a gel filtration media with a franctionation range of 200–2,500 daltons)

The active fractions recovered are chromatographed on CM-TRISACRYL® (agarose with acrylamide links, a gel filtration media with a fractionation range of 200–2,500 daltons) equilibrated in a buffer of pH 4.2, particularly a 0.04 M sodium acetate buffer.

Preferably, the active fractions are dialysed beforehand against the acetate buffer, then placed on the CM-trisacryl® (agarose with acrylamide links, a gel filtration media with a fractionation range of 200–2,500 daltons) column, and rinsed with the same buffer.

In order to remove the albumin, a first buffer of pH 5, 0.1 M is used, which operation may be carried out in 1 hour. The use of a second buffer, pH 4.2, 1 M, allows the majority of the SCLs to be eluted. This operation may be carried out within about 20 minutes. Before bringing the active fractions into contact with a sugar, it is advantageous to carry out dialysis to remove the dialysable molecules using a 0.01 M Na phosphate buffer, pH 7.2.

4—Affinity chromatography using a sugar as ligand:

The sugar constitutes the ligand of an agarose gel affinity chromatography column, particularly hexamethylenediamine polyacrylamide-agarose.

The gel is first washed with a 0.5 M buffer, for example NaCl, then with distilled water and finally centrifuged at low speed so as to remove non-adsorbed substances. A sugar solution, pH 4, for example 0.1 M N-acetylneuraminic acid, is added to the gel followed by a solution of an agent such as a carbodiamide.

The pH is advantageously kept at a value of the order of 4.5 and 5 at ambient temperature for about 1 hour, then gentle agitation is carried out for 10 to 15 hours.

The gel is washed several times to remove non-retained impurities.

For example, washing takes place with 1 M NaCl, then with 0.1 M acetic acid, and finally twice-distilled water.

The column packed with this preparation, is equilibrated to pH 7.2. The use of a 0.01 M sodium phosphate buffer has proved to be suitable.

The active sample of the previous stage is placed on the column and is advantageously equilibrated beforehand with the phosphate buffer.

After the column has been rinsed with this buffer, elution is carried out with at least two buffers, one for eluting the SCL and the other for removing the other proteins and regenerating the column.

The first buffer (I) is advantageously composed of a 0.01 M solution of sodium phosphate pH 7.2 containing 0.15 M NaCl. It leads to a peak containing the majority of the SCL. The second buffer (II) also contains ethylene glycol, particularly in a quantity of about 40 to 60%, preferably 50%. It leads to another peak containing the majority of the impurities.

The column is then rinsed with the sodium phosphate buffer.

5—Verifying the purity

The SCL recovered is analysed by HPLC using a conventional water/acetonitrile/trifluoroacetic acid system and the fraction corresponding to the main peak is then analysed by SDS-PAGE.

The invention thus gives methods of isolating very high purity products and of providing a product from which practically all the albumin has been removed.

The study of the purified SCLS thus obtained and of the SCLs corresponding to the expression products of the nucleotide sequences defined above shows that they possess lectinic properties of great interest.

1. These SCLs do not act directly on interferons but inhibit the synthesis of the secondary effector proteins induced by interferons.

The number of these effector proteins induced varies from one interferon isoform to another Moreover, the same molecular form does not necessarily induce the same effector proteins from one cell to another. By inhibiting the synthesis of all the IFN-dependent secondary proteins, the SCLs restore the cell to its initial state. Consequently, the cells regain their capacity to respond to growth stimuli which would otherwise be inhibited by the interferons.

2. The direct stimulation of growth is obtained in the absence of serum and affects a large number of cells, whether or not they are immunocompetent. This stimulation is obtained without a retro-inhibition effect which results in the development of the state whereby the cells are unaffected by repeated inductions of this substance.

Consequently, unlike conventional immunostimulants, the SCLs of the invention may be administered. repeatedly, if necessary in association with specific growth factors with which they may act synergistically. An example is interleukin-2 (Il 2) which is unable to stimulate the proliferation of T lymphocytes unless these lymphocytes are activated beforehand by a lectin or another antigen. Sarcolectin could thus act as a physiological activator of the receptors of Il 2. In other examples, sarcolectin will be associated with various interleukins or growth factors with a view to targeted amplification of growth due to the resulting synergy.

3. The mechanism of carcinogenesis seems to be clarified at least in part. It is generally assumed that the malignant transformation is the result of a process which, in progressive stages starting from benign proliferation, ends in the selection of highly carcinogenic cells. The protooncogenes are genes which are involved in the normal process of proliferation either as the growth fact or as the corresponding receptor, or by taking part in the metabolic chain involved in the growth process. The SCLs of the invention, more particularly the SCLs corresponding to SEQ ID NO: 3 or SEQ ID NO: 4 or the derived sequences are involved in initiating the synthesis of the cell DNA preparing the action of specific growth factors. In particular, the 55 kd SCL described above is a constitutive glycoprotein which is secreted in the extracellular medium and stimulates growth in a non-specific manner. As the effect of sarcolectins and growth factors is additive, it may be regarded as a co-oncogene, on the one hand due to its own effect on cell proliferation and its synergy with growth factors, and on the other hand due to its inhibiting effect on the anti-proliferative functions of interferons. As with all lectins, the biological functions of sarcolectin are inhibited by specific sugars.

In view of the properties reported above, the invention relates more particularly to the following applications of SCLs.

The invention therefore relates to their use as growth co-factors, for contributing to tissue growth and in particular for contributing to the regeneration of damaged tissues and to the acceleration of wound healing.

In this respect, they constitute highly effective therapeutic agents of local or general application.

As growth factors, they may be used for cell cultures in vitro.

In this respect, the particularly preferred products are constituted by human recombinant SCLs.

Indeed, when lymphocytes freshly removed from a healthy individual are cultivated, it is possible to stimulate their proliferation in the presence of interleukin-2.

After successive runs in the H1 medium without serum, the cells replicate in the presence of only Il2. However, the only protein secreted in the medium is SCL rn in a dimer form.

In H9 continuous T lines, cellular multiplication is assured by the SCL produced by the cells and secreted. In fact, in both cases, it is the only major protein detected in the medium by SDS-PAGE and Western blotting.

Tests carried out with the addition of SCL in an appropriate quantity show its favourable effect on cell growth.

The invention therefore also relates to the use of SCLs as therapeutic agents for stimulating the immune system, particularly as a stimulant of specific immunity; if necessary, the SCLs are used in association with an antigen, for example, with a growth factor such as interleukin.

As physiological activators of the proliferation of T lymphocytes, SCLs are therefore able to activate the synthesis of receptors for interleukins (Ils), particularly Il2. The continuous expression of SCLs in the cell appears to inhibit the state whereby the cells are unaffected by repeated inductions of interferon, leading to the continuous production of interferon on each induction, though the cells are incapable of expressing IFN functions.

The invention relates in particular to their use in treatments with interferon by taking advantage of their effect of inhibiting the synthesis of secondary effector proteins in such a way as to restore the cell to its initial state and restore its normal sensitivity to interferon.

The SCLs or their inhibitors are thus advantageously used in protocols for the repeated administration of IFN, for treating pathological states of infectious origin, for example, during the final stages of AIDS infections or during auto-immune diseases such as lupus erythematosus.

In certain competent cells, in particular those of PBL, the addition of recombinant SCL causes an agglutination and the synthesis of interferon of type 1 or 2.

The SCLs of the invention may also be used as vaccination adjuvants due to their ability to increase the proliferation of immunocompetent cells.

According to another aspect, the invention relates to the use of the SCLs of the invention as tools for identifying compounds that inhibit natural sarcolectins.

In particular, the invention relates to the use of SCLs for selecting compounds that inhibit their lectinic activity by competition, the antibodies or sugars, or also antagonists such as butyric amino acids or other butyroids.

In the different therapeutic uses mentioned above, the SCLs are, if necessay, fixed to albumin with a view to stabilization, to produce a delayed-action vehicle or to facilitate their diffusion in tissues and the expression of their functions.

The medicinal products developed from the inhibitory compounds mentioned above, which contain efficacious quantities of these compounds for obtaining the inhibition of interest, in association with pharmaceutical excipients, also fall within the scope of the invention.

Inhibitory sugars are specific sugars present on the cell membrane. They are simple or compound sugars such as N-acetylgalactosamine, sodium galacturonate, acetylated sugars such as N-acetylneuraminic acid, alpha or beta lactose, galactose, neuramine lactose These sugars, by fixing on the cell membrane, interfere with the fixation of SCL. On the basis of these observations, complex butyric derivatives can be obtained by fixing galactose, lactose, NANA, glucosamine, galactosamine, N-acetyl galacturonic acid on these butyric derivatives or on other butyric derivatives such as esters containing, for example, octal butyrate or PEG butyrate. (PEG= polyethylene glycol).

On the whole, the majority of these inhibitors indirectly increase the expression of induced interferons, increase the expression of endogenous interferon during different phases of normal growth or the process of tumorigenesis.

The butyroids can be used as growth inhibitors; they produce an interferon-like effect, but by different mechanisms. Their effect is not inhibited directly by SCLs, but acts as an antagonist effect of SCLs by different mechanisms.

The butyric derivatives formed from hydrophobic-hydrophilic amino acids such as 1-valine t-butyl ester, by their hydrophilic functions, fix to the cells and by their hydrophobic functions, maintain the molecules in contact with the membrane.

The butyric amino acids include alpha aminobutyric acid, alpha aminoisobutyric acid and gamma aminobutyric acid (GABA). These compounds have a high affinity in particular for the transformed cells and inhibit graft taking of Sarcomes TG180 cells (or of other cells) in mice.

As a result of these inhibitors or antagonists, excessive or continuous anti-physiological production of interferons may be re-equilibrated (by inhibiting the action of SCLs or by opposing their effects using antagonists) in order to combat immune disorders induced by certain chronic viral infections (HIV) or immune diseases.

The inhibitory compounds are capable of increasing considerably the antiviral resistance induced by IFN and are used to advantage in protocols including treatments with IFNS. They may also be used in anti-cancer therapies.

The invention relates in particular to the use of these inhibitors in such treatments in association with immuno-modulators such as *corynebacterium parvum* that SCL may replace if there is no constituent production of SCL.

Other products capable of inhibiting the activity of the SCLs of the invention by competition are composed of antibodies. These polyclonal or monoclonal antibodies directed against the SCLs of the invention are produced advantageously according to conventional methods. As novel products, they are a further object of the invention.

In therapeutics, the anti-SCL antibodies of the invention are particularly valuable agents for inhibiting the effects of the SCLs produced in excess in pathological states such as cancers, chronic viral or auto-immune diseases.

The medicinal products developed from these antibodies are characterised in that they contain an efficacious quantity of these antibodies for the applications envisaged, in association with an inert pharmaceutical vehicle.

These medicinal products are particularly suitable for anti-tumour treatments.

In diagnostics, these antibodies may be used for all the immunological reactions, particularly ELISA and Western blots, and make it possible to determine qualitatively and quantitatively the presence of SCL in a biological extract taken from a patient.

The invention thus relates to a method for detecting in vitro SCLs, and more particularly the 55 kd SCL as purified according to the methods described above, or corresponding to the protein expressed by SEQ ID NO: 1, or obtained by synthesis.

Said method comprises:
bringing a biological sample to be analysed originating from a patient or cells into contact with an anti-SCL antibody preparation or a Fab fragment immobilised on a solid support under suitable conditions for the production of an antigen-antibody complex with the SCLs if they are present in the sample or cells, then, detecting the formation of such a complex of the antigen-antibody type, advantageously by operating according to usual methods.

For example, cytofluorometry methods are used.

This method of detection makes it possible to detect with great sensitivity and at high speed the presence of SCL in the sample tested, and to detect any reaction of an antigen-antibody type.

The invention also relates to a kit that can be used to carry out this detection. This kit is characterised in that it comprises:
a suitable solid phase acting as a support,
an anti-SCL antibody preparation or Fab fragments, free or immobilised,
buffer solutions and suitable reagents for the immunological reactions and for the detection reactions.

The antibodies used in these methods and kits are advantageously antibodies directed against the peptides SEQ ID NO: 5 defined above or their derivatives.

As a variant, the detection relates to the presence of genes coding for the SCLs and comprises
carrying out the stage of bringing the biological sample to be analysed or cells originating from a patient into contact with a probe as defined above under suitable conditions for the production of a hybridisation complex, if the genes coding for the SCLs are present in the sample or cells,
detecting the hybridisation complex and quantifying the expression of the SCLs by these genes.

The invention also relates to a kit that may be used in this method and comprises said probes and the buffer solutions and useful reagents for performing the hybridisation reaction.

Other inhibitors of the SCLs of the invention are composed of the antisense nucleotide sequences defined above. These antisense sequences are able to block the expression of SCL, for example, in the case of osteogenic sarcomas.

Other applications for the SCLs according to the invention are based on their ability to agglutinate cells and their affinity for simple sugars.

These properties are turned to good account in diagnostics or therapeutics.

Other characteristics and advantages of the invention will be given in the examples that follow.

BRIEF DESCRIPTION OF THE DRAWINGS

Reference is made to FIGS. 1 to 5 which represent, respectively.

DESCRIPTION OF THE PREFERRED EMBODIMENTS

EXAMPLE 1

Procedure for the Purification of Sarcolectin

Figure 1:
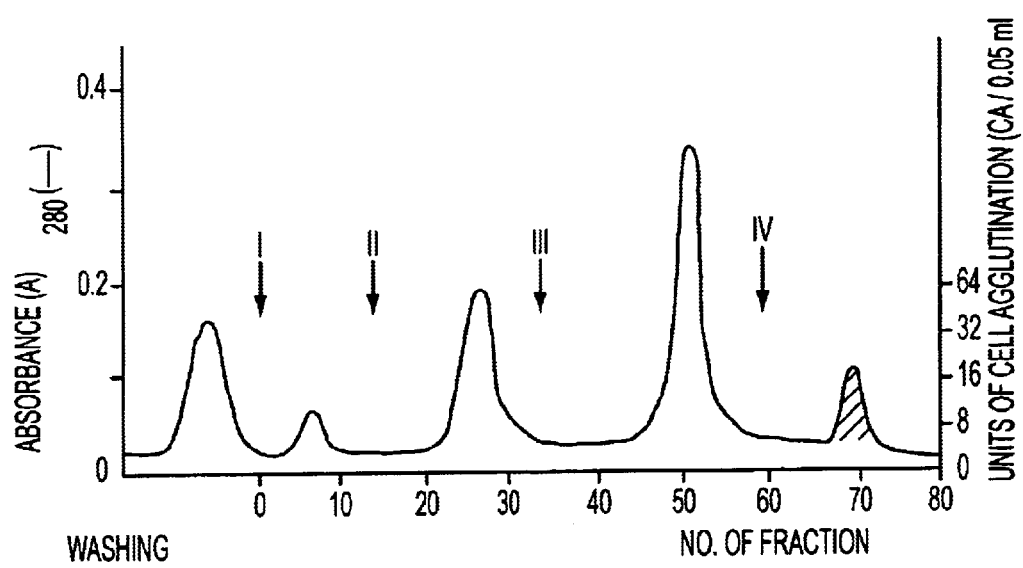
FIG. 1: the elution profile of the SCL fractions chromatographed on DEAE-cellulose, obtained after chromatography on SEPHACRYL® (agarose with acrylamide links, a gel filtration media with a fractionation range of 5,000–250,000 daltons for globular proteins) of tissue extracts treated beforehand.

The scheme for this procedure is as follows:

Stage I—Preparation of the biological material and freeze-drying.

Stage II—Hydration of the material and pretreatment either with pepsin or at pH 5.

Stage III—Chromatography on SEPHACRYL® (agarose with acrylamide links, a gel filtration media with a fractionation range of 5,000–250,000 daltons for globular proteins) S-200.

Stage IV—Chromatography on ion exchange resin: DEAE-cellulose or CM-TRISACRYL® (agarose with acrylamide links, a gel filtration media with a fractionation range of 200–2,500 daltons)

Stage V—Affinity chromatography on sugar

Stage VI—Reversed-phase HPLC (for sequencing):

C18 column $H_2O$/acetonitrile gradient

C4 column $H_2O$/acetonitrile gradient

I) Preparation of the biological material and freeze-drying

The tissue samples are washed carefully in minimal Eagle medium until all traces of blood have been removed and are then freeze-dried and kept in the dry state at −20° C. The dry tissue is then finely chopped to obtain a powder which is weighed, hydrated in MEM medium (to which antibiotics have been added) to a concentration of 6% (dry weight in g). The suspension is agitated at +4° C. for 20 h, centrifuged at a low speed of 4000 rpm for 20 min for clarification, then centrifuged at 27,000 rpm for 2 h at 90,000 g (it is advantageous to use a Spinco L3 ultracentrifuge).

The supernatant which contains sarcolectin is collected after filtration over sterile gauze and over a 1.2 millipore filter, distributed into 2.5 ml pill boxes, then freeze-dried before storage at −80° C.

II) Hydration of the material and pre-treatment

At the time of use, the freeze-dried product is hydrated in 2.5 ml of twice-distilled water and then dissolved thoroughly.

The preparation then undergoes either a treatment with pepsin or a treatment at pH 5 (isoelectric point of SCL).

A) Treatment with pepsin

It has been ascertained that a controlled treatment with pepsin makes it possible to retain the physical-chemical characteristics (migrations in the gel) and does not destroy the biological activity of the tissue extracts, but does destroy other proteins contaminating the preparations.

The tissue extracts (concentration 6%) are treated with a solution of pepsin crystallised twice (2,675 units/mg) to a final concentration of 1 mg/ml. The reaction mixture is adjusted to pH 2 (optimum pH of pepsin activity) and incubated at 37° C. for 2 h; a substantial precipitate forms. The enzyme action is then stopped by adjusting the pH to 7.3 and adding Iniprol (Choay) $10^5$ units/mg protease, for one night at 4° C.

The sample is centrifuged and the supernatant removed is then filtered over SEPHACRYL® (agarose with acrylamide links, a gel filtration media with a fractionation range of 5,000–250,000 daltons for globular proteins) S-200 gel.

B) Treatment at pH 5

The preparation of tissue extract is adjusted to pH 5 by adding 1N HCl, then left at room temperature for 15 min. A substantial precipitate appears which is centrifuged at 4,000 rpm for 15 min. After being decanted, the supernatant represents the sample for the filtration stage over SEPHACRYL® (agarose with acrylamide links, a gel filtration media with a fractionation range of 5,000–250,000 daltons for globular proteins S-200 gel.

III) Chromatography on SEPHACRYL® (agarose with acrylamide links, a gel filtration media with a fractionation range of 5,000–250,000 daltons for globular proteins) S-200

The column used (Pharmacia 2×30 cm) contains SEPHACRYL® (agarose with acrylamide links, a gel filtration media with a fractionation range of 5,000–250,000 daltons for globular proteins) S-200 gel (Pharmacia) swollen beforehand in buffer. The sample is introduced into the column in a volume of 2 5. ml, the rate of flow of the eluant (PBS) is 20 ml per hour and the volume of each fraction is 1.35 ml. The determination of the molecular weight of the filtered sample is calculated by reference to a range of proteins of known molecular weights.

The estimate of the molecular weight is based on the linear relationship that exists between the effluent volume (Ve) and the logarithm of the molecular weight.

The biological activity (agglutination capacity of the cells) of each fraction is then tested. On the basis of the effluent volume of the fraction which presents the maximum biological activity, it is possible to determine the molecular weight, after reference to the calibration curve, which is between 190 and 200 kd.-

IV) Chromatography on ion exchange resins DEAE cellulose

A column is packed with diethylaminoethyl cellulose (DEAE 52, Whatman, England) swollen beforehand and equilibrated in the following buffer, pH 7.6: 20 mM NaCl, 0.1 mM EDTA, 15 mM β-mercaptoethanol, 20 mM tris-acetic acid. The sample (pool of the biologically active fractions obtained after filtration over SEPHACRYL® (agarose with acrylamide links, a gel filtration media with a fractionation range of 5,000–250,000 daltons for globular proteins) S-200) is introduced into the column which is then rinsed carefully with the same buffer.

The proteins are eluted for 4 h in the presence of buffer to which NaCl with a molarity ranging from 0 to 0.5 M has been added, representing a linear gradient from pH 7.6 to 4.0. The rate of elution is 20 ml/hour. The profile recorded is shown in FIG. 1. Peak III contains albumin and traces of SCL whilst peak IV (hatched) corresponds to the biological activity and contains the majority of the SCL. The latter is eluted with a 0.25 M sodium buffer.

This stage may be replaced by chromatography on a Mono Q column using HPLC (gradient: 20 mM L-histidine pH 5.5–6.0/1M NaCl.

CM-TRISACRYL-M® (agarose with acrylamide links, a gel filtration media with a fractionation range of 200–2,500 daltons)

A pharmacia column (1×15 cm) is packed with CM-TRISACRYL-M® (agarose with acrylamide links, a gel filtration media with a fractionation range of 200–2,500 daltons) (IBF France) then equilibrated in a 0.04 M sodium acetate buffer, pH 4.2.

The sample containing the active fractions of sarcolectin is dialysed beforehand against the 0.04 M acetate buffer, pH 4.2, then placed on the column which is then rinsed with the same acetate buffer for 1 h.

Figure 1A:
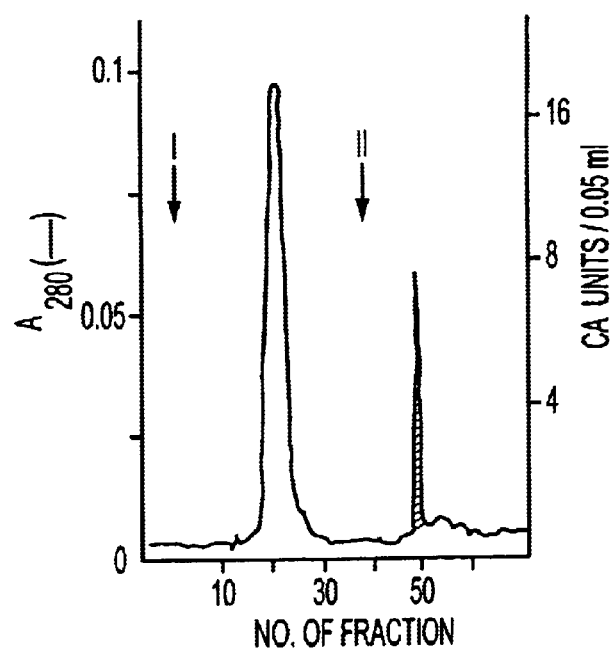
FIGS. 1A and 1B: the elution profiles on CM-TRISACRYL® (agarose with acrylamide links, a gel filtration media with a fractionation range of 200–2,500 daltons) of biologically active fractions of SCLs collected on DEAE-cellulose.
Figure 1B:
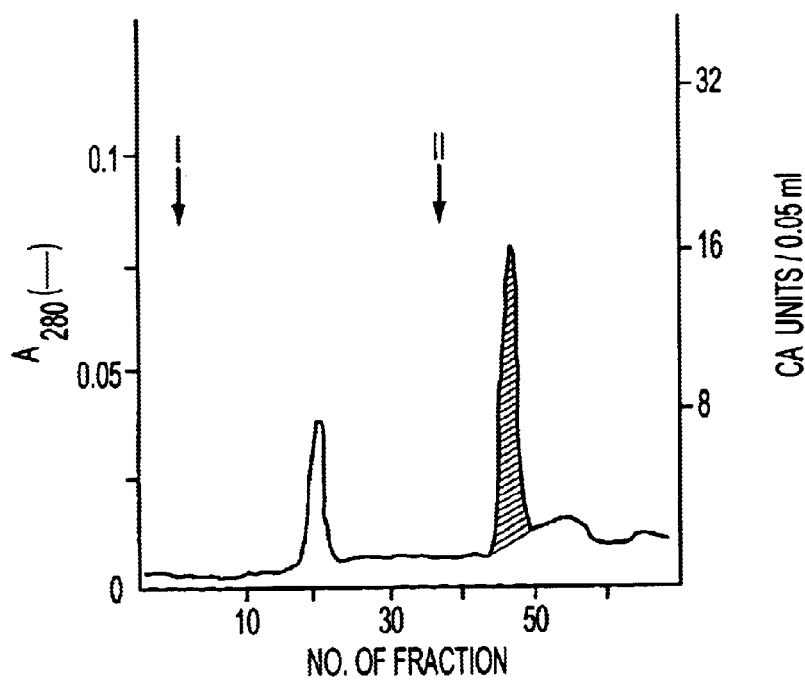

The elution profile contains two buffers:
the first buffer: 0.1 M sodium acetate, pH 5, which removes mostly albumin; elution takes about 1 hour; (see FIG. 1A where peak 15 contains albumin and peak 50 (hatched peak) contains SCL, expressed in cytoagglutinating activity (CA).
the second buffer: 1 M sodium acetate, pH 4.2, which elutes mostly sarcolectin; elution takes 20 minutes (4 min/fraction) (see FIG. 1B).

Fractions 40–50 contain sarcolectin and are dialysed against the 0.01 M Na phosphate buffer, pH 7.2, which will be used for the next stage.

V) Affinity chromatography, using N-acetylneuraminic acid as ligand (abbreviated to N.A.N.A.).

9 ml of Ultragel-HMD-Aca 34, IBF code 2461 61 (hexamethylene-diamine polyacrylamide agarose) are washed 3 to 4 times in 25 ml of 0.5 M NaCl buffer, then at least twice with twice-distilled water and finally centrifuged at low speed.

4 ml of a 0.08 M solution of N-acetylneuraminic acid (type IV, Sigma) adjusted to pH 4.7 are added to the gel.

5 ml of 0.1 M EDCL, pH 6 (1-ethyl-3,3-dimethyl-aminopropyl-carbodiamide, Sigma) are then added and the pH is kept between 4.5 and 5 for 1 h at the temperature of the laboratory. The mixture is then kept under gentle agitation for one night. The gel is washed several times with 1 M NaCl then with 2 volumes of 0.1 M acetic acid and rinsed with twice-distilled water. A Pharmacia column (1×15 cm) is packed with this preparation and equilibrated with the 0.01 M Na phosphate buffer, pH 7.2. The sample of sarcolectin which has been equilibrated beforehand with the Na phosphate buffer is introduced and recycled three times. After the column has been rinsed with the same buffer for 1 h, the non-retained impurities are removed and elution is then carried out with two buffers:

buffer $E_1$=0.01 M sodium phosphate, pH 7.2,+0.15 M NaCl which elutes sarcolectin (hatched peak in FIG. 2A) as indicated by O. D. recording, and determination of the biological activity (agglutination of the cells by operating as described in (8));

buffer $E_2$=0.01 M sodium phosphate, pH 7.2,+0.15 M NaCl +50% ethylene glycol to remove the other proteins (peak between 15 and 20) and regenerate the column.

Figure 2A:
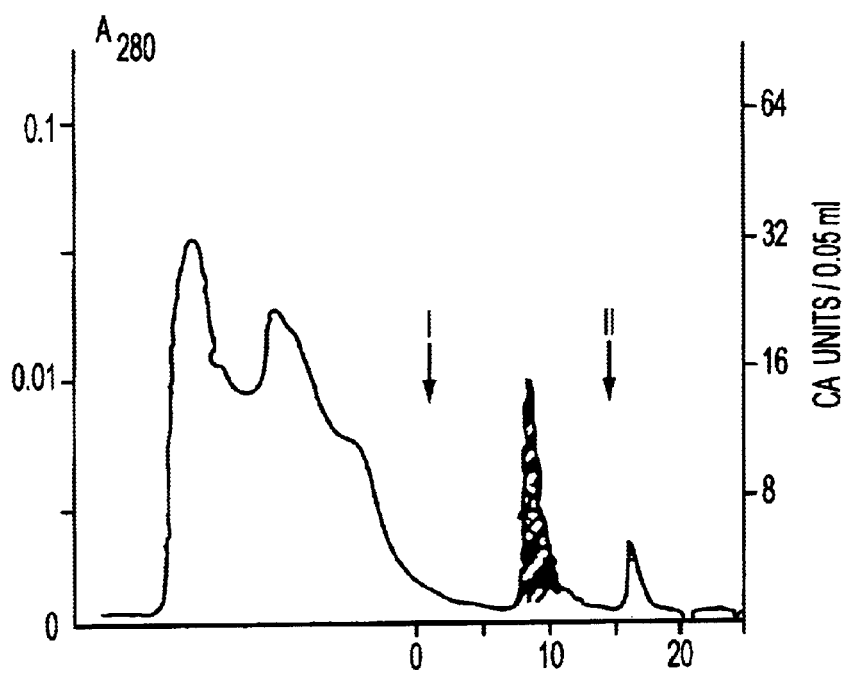
FIGS. 2A and 2B: the elution profiles of the fractions obtained by chromatography with a sugar as ligand, and analysis of the active fraction by reversed-phase HPLC, FIGS. 3A and B: verification by an SDS-PAGE gel of the various purification stages and the Western blot using anti-65 kd and anti-55 kd antibodies.

The column is then rinsed with the 0.01 M sodium phosphate buffer, pH 7.2 (FIG. 2A).

(VI) Reversed-phase HPLC

The apparatus used is an "HPLC Controller 2152", LKB brand, and reversed-phase separation is carried out with a C18 column (Waters).

The conventional water/acetonitrile/trifluoroacetic acid, 0.1%, system is used with detection at 220–280 nm.

The gradient is programmed as follows:

| Time | Delivery | % acetonitrile |
|---|---|---|
| 0 | 1 ml | 0 |
| 40 | 1 ml | 50 |
| 60 | 1 ml | 80 |
| 70 | 1 ml | 80 |
| 80 | 1 ml | 0 |

Figure 2B:
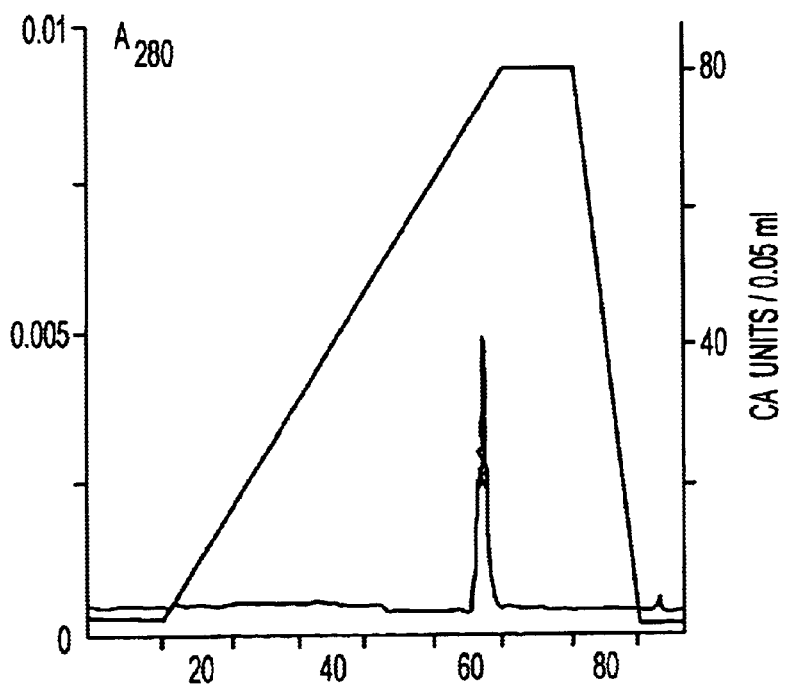

A major peak situated at 75% of the acetonitrile gradient is recorded (FIG. 2B).

The corresponding SDS-PAGE fraction is analysed by SDS-PAGE gel. The Western blot shows the three bands using the anti-55 kd serum: at 65 kd, 55 kd and ≦14 kd. The use of the anti-65 kd serum is prevented by the fact that it is constantly contaminated by albumin.

Results Obtained

The various stages of purification are monitored with respect to two characteristic functions of the SCLS, namely their capacity 1) to stimulate the synthesis of DNA in human H9 T cells, cultivated in a medium without serum for 24 h and 2) to agglutinate cells. The results of the last 3 purification stages are shown in Table 1, indicating the count per minute (cpm) of $^3$[H] thymidine, the percentage stimulation and cell agglutination (unit/0.05 ml).

TABLE 1

| Purification stage | cpm $^3$[H] thymidine | Stimulation (%) of DNA synthesis | (%) Cell agglutination unit/0.05 |
|---|---|---|---|
| DEA cellulose | 6,728 ± 717 | 63.5 | 16 |
| CM-TRISACRYL ® (agarose with acrylamide links a gel filtration media with a fractionation range of 200–2,500 daltons) | 10,525 ± 1,833 | 155.8 | 16 |
| NANA affin. chromatog. | 8,686 ± 1,791 | 111.1 | 16 |
| ref. H9 cells | 4,141 ± 717 | — | — |

An examination of these results shows that the last three purification stages result in a practically pure protein being obtained.

On the basis of the initial protein level, purification is of the order of 16,500 fold. The purified protein obtained at the end of the procedure described above gives a single peak after analysis by HPLC.

Figure 3A:
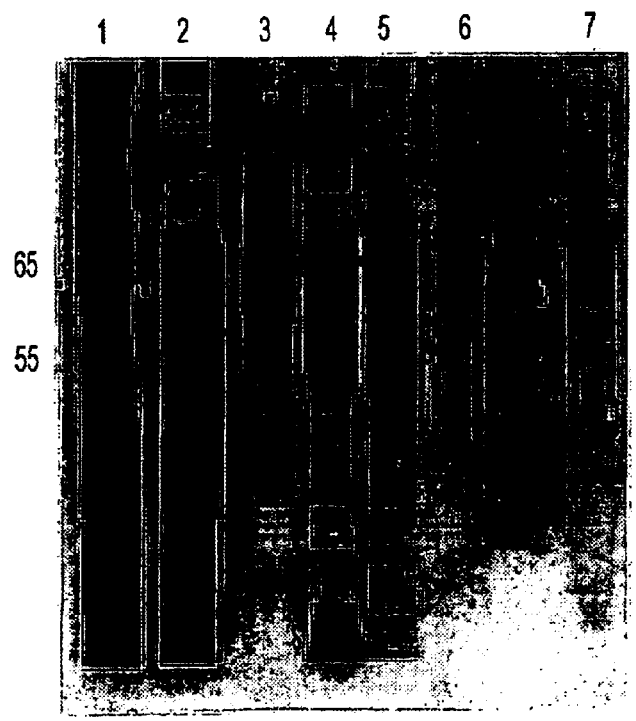

The capacity to agglutinate these same cells is found to remain unchanged. After chromatography on SDS-PAGE gel stained with silver nitrate and denaturation, three characteristic bands are observed, the size of which was estimated successively at 65 kd, 55 kd and $\leq$14 kd. (See slope 7 in FIG. 3A where the other slopes correspond to the various stages of purification verified by SDS-PAGE, namely chromatographies 1) on SEPHACRYL® (agarose with acrylamide links, a gel filtration media with a fractionation range of 5,000–250,000 daltons for globular proteins) S-200, 2) on DEAE-cellulose, 3) on CM-TRISACRYL® (agarose with acrylamide links, a gel filtration media with a fractionation range of 200–2,500 daltons) (peak 1 of albumin), 4) is a size reference point, 5) corresponds to chromatography on CM-TRISACRYL® (agarose with acrylamide links, a gel filtration media with a fractionation range of 200–2,500 daltons) (peak 2 of SCL), 6) to affinity chromatography with NANA and 7) to HPLC).

These bands were cut out, freeze-dried, ground and injected into rabbits for immunisation.

Figure 3B:
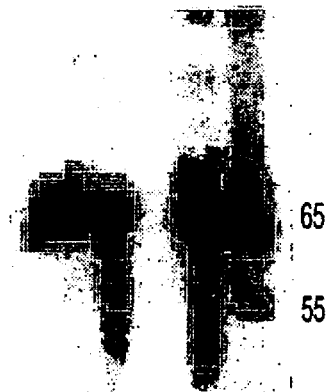

Due to the proximity of their size and their similar physical-chemical properties, anti-65 kd serum also reacts with albumin. On the other hand, anti-55 kd serum seems to be completely homogeneous. Both anti-65 kd serum and anti-55 kd serum recognise the proteins of the two other molecular weights after analysis by Western blotting (FIG. 3B), where slopes 1 and 3 correspond to the use of anti-65 kd antibodies and slopes 2 and 4 to that of anti-55 kd antibodies.

EXAMPLE 2

Rapid Method of Purification

A rapid purification may be obtained for certain biological extracts for diagnostic purposes (for example, serum diluted to one tenth) by proceeding as follows:

Lowering the pH of the medium to pH 5 for 30 minutes;

A substantial precipitate is noted in this case, which will be removed by centrifugation;

Readjustment to pH 7.4; the supernatant contains 65 and 55 kd proteins which can be recognised by the Western blots with the aid of specific antibodies. The titre may be estimated by ELISA using the same antibodies.

Figure 4A:
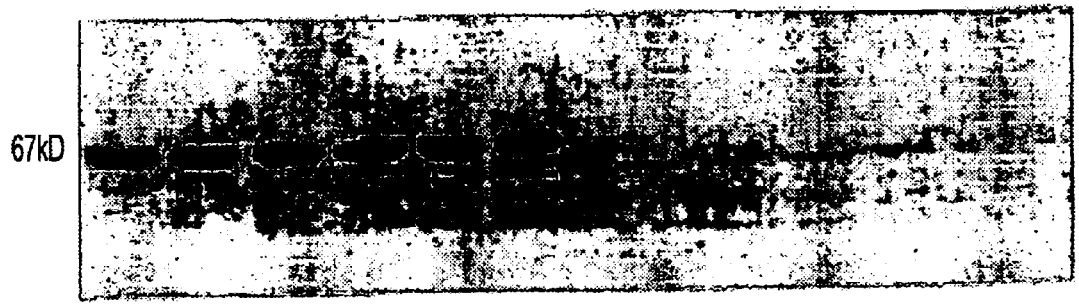
FIGS. 4A and 4B: a photo of an SDS-PAGE electrophoresis of an SCL preparation before and after controlled treatment with pepsin, and a Western blot showing the reaction of anti-65 kd monoclonal antibodies with the protein of the invention and albumin respectively.
Figure 4B:

In vivo, SCLs strongly bound to albumin are found—a fact which was unknown until now. Using monoclonal antibodies, clearly detectable bands of this protein may be detected by Western blotting (see FIG. 4A; SDS-PAGE electrophoresis stained with coomassie blue). Beneath the major band of 67 kd containing albumin there is a minor band of 65 kd. The controlled treatment of the preparation with pepsin digests the albumin but retains the minor band; FIG. 4B: the Western blot using the same preparation marks intensely the minor band of 65 kd. Note the diffusion of the marker on the albumin which is only indirectly marked by the 55 kd protein.

These results were fundamental to countering the interpretation which prevailed regarding the identity of the band of 65 kd. Thus the invention allowed the revelation that this molecule is indeed an artifact linked to the fixation of some SCL molecules of 55 kd on albumin. In FIGS. 4a and 4b attached to this text, this observation is clearly illustrated. It is also supported by the article of FU YUE ZENG et al. (12) in which the 5' sequence of the SCL protein is considered as containing analogues grown with albumin.

Similarly, using culture media which allow the growth of the cells without serum, a single protein band identified as being SCL is detected, secreted by the cells: simian Vero, human osteogenic sarcomas, T lymphocytes from PBL, or H9 cells in a continuous culture. In these cultures containing few proteins, SCL must play an important part in regulating growth.

EXAMPLE 3

Cloning and Identification of the Gene of Human Sarcolectins

The bank of CDNA used is of commercial origin derived from 34-week human placenta. These CDNA were cloned at the EcoRI site of the galactosidase gene of the gt 11 lambda phage.

The selection was made using anti-sarcolectin antibodies in parallel, obtained separately against the 65 kd protein and the 55 kd protein as described in Example 1. To summarise, the bands were isolated and cut out, freeze-dried and crushed and then used to immunise rabbits.

The anti-65 kd serum recognises the corresponding protein and also to some extent albumin. On the other hand, the anti-55 kd antibody appears to be specific. The two antibodies were used in parallel in a well defined order. Table 2 gives a summary of the methods adopted for isolating 4 clones.

TABLE 2

| | Number of selections | | | | |
|---|---|---|---|---|---|
| | 1 | 2 | 3 | 4 | C/C |
| 1 | 1a | 2a → 0 | | | |
| | | 2b → 0 | | | |
| 2 | 1a | 2a → 0 | | | |
| | | 2b → 0 | | | |
| 3 | 1a | 2a → 0 | | | |
| | | 2b → 0 | | | |
| 4 | 1a | 2a → 0 | | | |
| | | 2b → 0 | | | |
| 5 | 1a | 2a → 0 | | 4b | Clone 5 |
| | | 2b → + | → 3b | 4b | |
| 6 | 1a | 2a → 0 | | 4b | Clone 6 |
| | | 2b → + | → 3b | 4b | |
| 7 | 1a | 2a → 0 | | | |
| | | 2b → 0 | | | |
| 8 | 1a | 2a → 0 | | | |
| | | 2b → 0 | | | |
| 9 | 1a | 2a → 0 | | 4b | Clone 9 |
| | | 2b → + | → 3b | 4b | |
| 10 | 1a | 2a → + | → 3a | 4b | Clone 10 |
| | | 2b → 0 | | 4b | | a: Anti-65 kd antibodies
b: Anti-55 kd antibodies

Identification of clones

The bank was enlarged to obtain approx. $10^5$ to $10^6$ clones. The empty clones produce galactosidase −1. They are stained blue after treatment with IPTG +X-gal. The cloned genes are inserted at the EcoRI site of galactosidase and the fusion protein thus obtained is colourless. The colourless colonies are then treated with specific sera to which are added an anti-rabbit antiserum coupled with peroxidase visualised by DAB, which enables them to be visualised.

As set out in Table 2, 10 clones were isolated during the first run by virtue of the specific antibody (a).

During the second run, half of the descendants of each isolated clone was sub-cloned by the anti-65 kd antibody (a) and the other half by the anti-55 kd antibody (b).

By using this procedure during the third cloning operation, a clone known as 5 was isolated by virtue of antibody b, a clone called 6 with antibody b, a clone 9 with antibody b, and finally a clone 10 with antibody a. This procedure therefore led to the isolation of a total of 4 clones.

In the fourth cloning operation, only the anti-55 kd antibodies (b) were used and all the clones obtained, whether isolated by antibodies (a) or (b) were recognised by antibody b which is much more specific, as indicated above. The analysis of the sequences shows that in fact 3 different clones are isolated, designated clones 5 and clone 6 since, after sequencing, clones 9 and 10 proved to be absolutely identical.

It will thus be noted that these three clones were isolated with the two different antibodies (a) and (b): their identity suggests antigenic relationships between the two sera, corresponding to epitopes shared by the proteins. These proteins may therefore represent members of one family.

Results obtained with clone 5

Structure and characterisation of the clone

The CDNA isolated has a length of 1.8 kb. It contains an open reading frame of 1 407 bp which contains the genetic information for 469 amino acids. Its structure is given in SEQ ID NO: 1. The ATG initiation and TGA termination sequences are in position 62 and 1469 respectively.

EXAMPLE 4

Study of the 55 kd Protein

1) Two kinds of cell lines originating from reference human osteogenic sarcomas (MG 63) or HOS were cultivated. The culture of these cells was carried out in the presence of 1% foetal calf serum and RPMI medium. The proteins secreted in the medium after purification according to the procedure of Example 1 were analysed. After Western blotting, a band of 65 kd and a band of 55 kd were obtained. Both proteins were secreted in the culture medium.

2) In a second series of experiments, these same cells were cultivated in a synthetic Whittaker medium (Ultra Doma MDCK) without serum, during two successive runs, so as to remove all residual albumin. In total, these media contain only very few proteins (2–5 ng/ml). The cells secrete lectins capable of agglutinating the H9 cells (T lymphocytes in a continuous line treated with 10% formaldehyde). After Western blotting (using both monospecific antibodies against the 55 kd protein and the commercial monoclonal antiserum against type 7 cytokeratin), a single band was obtained in the 55 kd region. This is the only band that can be detected after SDS-PAGE and staining with coomassie blue, recognised both by anti-55 kd sera and by commercial mesothelial anti-cytokeratin monoclonal antibodies. It is possible, therefore, that the 55 kd protein, possibly with the aid of its lectinic functions, is capable of being fixed to albumin, thus giving the SCL the appearance of having a higher molecular weight that it actually has.

This hypothesis is also supported by the fact that a second band with a slightly lower mol. weight is detected in highly purified (99%) commercial bovine albumin with the aid of the commercial monoclonal antiserum. After treatment of the albumin preparation with pepsin, this band persists, whereas the albumin is digested (see FIGS. 4A and 4B). The relationship between albumin and SCL could be purely fortuitous, or it could be important for the diffusion of SCL in the organism, and for maintaining its stability.

3) In all the tests carried out, the majority of the SCLs are secreted in the culture medium, unlike the intermediate filaments which are generally intracellular.

4) On the whole, the protein sequences obtained may be shown diagrammatically as follows:

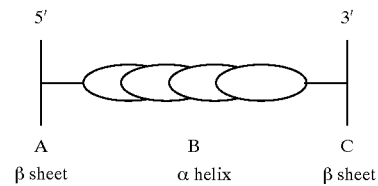

Domain A, corresponding to approx 320 bp in DNA is variable; it is translated into β sheet in the protein. This region contains 12 blocks 80 to 100% homologous with those found in the 14 kd lectin of the protein binding galactoside (140/320 bp). This domain contains the essential part of the lectinic function of the molecule. In total, at least 30 of these blocks are located mainly at the ends Domain B is formed from 4 α helixes. It possesses the following homologies for DNA:

56 kd human keratin: 78% homologous over a length of 814 bp.

Human vimentine: 52% homologous over a length of 625 bp

Human neurofilament: 55% homologous over a length of 589 bp.

Domain C contains short sequences translated into β sheet which also possesses lectinic sequences.

5) C. Glass et al (9) isolated a gene and classified this molecule as an intermediate filament under the name of mesothelial cytokeratin. This identification is based on the sequence analogies mentioned above and which relate to the stable α helixes of the molecule.

On the other hand, the invention establishes that the variable 5' segment forming the β sheet contains the lectinic function of the molecule. The stable domain of the four α helixes that occupy domain B seems to ensure the stability of the molecule. The biological significance of this 55 kd molecule is fundamentally different to that disclosed by the previous authors for the molecule they described. Moreover, the SCL of the invention, as indicated above, is secreted in the medium. This property is unusual for intermediate filaments which, as part of the cytoskeleton, have the essential role of contributing to the stability of the intracellular structure. The SCLs are expressed in the monomer form, or in certain cases the dimer form. The intermediate filaments, on the other hand, are polymerised to polymers.

6) The controlled treatment with pepsin at pH 2 of the purified SCL destroys the stimulating function of SCL without modifying either the migration or the size of the molecule in the SDS-PAGE gel. Similarly, the agglutinating power of the cells is retained. It is known, in fact, that pepsin first destroys the sites located at the level of the 5' end of the molecule (at the level of the aromatic amino acids threonine and tyrosine) which partly explains the loss of biological functions.

EXAMPLE 5

Study of Biological Activity

I—Study of the inhibiting effects of sugars with respect to SCL

Action of simple suaars on the agglutination of cells

A wide variety of cells originating either from rodents or from primates was tested. Agglutination is obtained by suspending the cells in an MEM medium in the absence of serum. The test may be carried out in two ways, either in the presence of a sarcolectin dilution range in a base 2 geometric progression, by identifying the concentration at which 50% of the cells are agglutinated, or by identifying the affinity of the various sugars for the cell receptors.

In the example shown, murine sarcolectin originating from the ascitic fluid of Swiss mice grafted with Crocker TG180 sarcoma contains 32 units agglutinating the H9 cells which originate from a T lymphoma, fixed by 10% formaldehyde.

The table below illustrates the affinity of the receptors for the various sugars in the presence of 2 agglutinating units.

| D galactose: | affinity | 0.28 mM |
|---|---|---|
| β lactose: | | 0.25 mM |
| α lactose: | | 0.125 mM |
| N.A.N.A: | | 0.0075 mM |

In the case of murine sarcolectin, the affinity is higher for β lactose than for α lactose, whereas the reverse is observed with SCLs originating from human placenta. The highest affinity for human tissues is N.A.N.A. Other inhibitor sugars include N-acetylglucosamine or galacturonate (mainly in the case of hamsters), this list being by no means exhaustive.

The inhibitory sugars not only prevent the agglutination of cells but also impede the various biological effects of sarcolectins, particularly growth stimulation.

This effect will be even more pronounced as the affinity for the SCL receptors increases.

An evaluation will therefore be made of the advantage of the SCLs of the invention which make it possible to select sugars with a very high inhibiting effect and whose indirect effect on growth can be turned to good account.

As has already been emphasised, this inhibiting effect of sugars with regard to SCLs makes it possible to increase the antiviral and antiproliferative functions of IFN.

Indirect antiviral effects of inhibiting suaars

The model used is the encephalomyocarditis virus (EMC) which kills mice in practically all cases after rather varying but relatively short incubation periods.

Male mice (average weight: 2.5 g, aged 8 to 10 weeks) were injected i.p. with sodium galacturonate, glucosamine and N-acetylneuraminic acid (5 to 10% solutions containing 100 mM sugar). 24 hours afterwards, one hundred lethal doses (50%) of EMC virus are injected by the same route. After one hour, murine interferon is injected (in a dose of 20,000 units in 0.5 ml). Table 3 gives the number of animals surviving out of the total tested, the percentage and statistical significance.

TABLE 3

Protection of IFN against the pathogenic effect of the encephalomyocarditis virus in Swiss mice (number of animals surviving out of the total number tested, percentage and statistical significance [*])

| Na galacturonate | | | | Na glucuronate (negative reference) | | | |
|---|---|---|---|---|---|---|---|
| +MEM | | +IFN | | +MEM | | +IFN | |
| 6/75 | 8% | 22/90a | 24% | 6/45 | 13% | 5/45 | 11% |
| Glucosamine | | | | Reference group | | | |
| +MEM | | +IFN | | +MEM | | +IFN | |
| 1/30 | 3% | 14/45b | 31% | 0/120 | 0% | 6/120 | 5% |
| N-acetylneuraminic acid | | | | | | | |
| +MEM | | +IFN | | | | | |
| 0/15 | 0% | 8/15c | 53% | | | | | ap 0.001; bp 0.01; cp 0.02 (compared with IFN)

An examination of these results shows that the use of SCL inhibiting sugars makes it possible to reduce the antagonistic effect of natural sarcolectins, the level of which increases because of the immunity stimulation due to the virus, leading to increased synthesis of macrophages with T lymphocytes.

In the mice treated only with interferon, only six animals out of 120 survive, whereas the increase in the total survival rate is very substantial when interferon is used in association with N.A.N.A., glucosamine or galacturonate.

By providing SCLs that serve as models for in vitro studies, the invention makes it possible to select those sugars that have the ihhibiting effect of interest and to develop medicinal products containing them as active ingredients in suitable quantities with a view to a highly efficacious antiviral treatment.

Antitumour action of sugars that inhibit SCL

The ability of inhibitory sugars to impede the stimulating effect of growth induced by sarcolectin may indirectly affect in vivo tumour development. As shown in vitro according to the invention, SCLs may act synergistically with growth factors and promote cell multiplication indirectly. Natural SCLs could therefore promote oncogenesis by blocking the effect of interferon.

An evaluation will therefore be carried out of the advantage of inhibiting the action of natural SCLs in order to promote the equilibrium of tissue development in favour of growth inhibitors.

In order to test the antitumour capacity of SCL inhibiting sugars, TG-180 tumour cells originating from a tumour resistant to chemical metabolic inhibitors was grafted. In a concentration of $3 \times 10^6$ cells injected i.p. into 20 gr Swiss mice, an ascitic tumour is obtained which is detectable in 10 days and kills practically 100% of the animals in 21–25 days.

In parallel series, the various groups of animals were treated 3 days after inoculation, either with a specific sugar (glucosamine, lactose, galacturonate, N.A.N.A., neuraminelactose) in a 5 to 10% solution, the sugar concentration being 100 mM, or with the same treatment in association with an injection of immuno-stimulant (extract of corynebacterium parvum, Merieux, France), in a dose of 200 g/mouse, or interferon, or both.

4 groups of mice per experiment were used.

The results obtained are given in Table 4. They are assessed by the percentage of tumours that appeared on the 10th day, the mean survival time of the animals (MST) in. days, and the final survival (as a percentage).

TABLE 4

| Sugar | No. of mice | Tumours on 10th day (%) | MST | Number | Final survival (%) |
|---|---|---|---|---|---|
| Medium | 105 | 94(89) | 19 ± 1 | 0 | (0) |
| +IFN | 105 | 65(68) | 25 ± 4 | 7 | (7) |
| +CP | 105 | 85(89) | 32 ± 5 | 10 | (10) |
| +CP +IFN | 105 | 43(41) | 60 ± 7 | 45 | (42) |
| Glucosamine | 15 | 3(20) | 28 ± 6 | 1 | (6) |
| +IFN | 45 | 6(13) | 39 ± 9 | 8 | (17) |
| +CP | 75 | 26(34) | 67 ± 8 | 40 | (53) |
| +CP +IFN | 60 | 17(28) | 70 ± 9 | 35 | (58) |
| Lactose | 30 | 11(36) | 26 ± 6 | 1 | (3) |
| +IFN | 45 | 9(20) | 64 ± 9 | 6 | (13) |
| +CP | 30 | 3(10) | 82 ± 13 | 14 | (46) |
| +CP +IFN | 45 | 6(13) | 75 ± 10 | 29 | (64) |
| Galacturonate | 15 | 3(20) | 31 ± 10 | 1 | (6) |
| +IFN | 15 | 6(40) | 34 ± 15 | 2 | (13) |
| +CP | 15 | 2(13) | 42 ± 16 | 3 | (20) |
| +CP +IFN | 15 | 1 (6) | 81 ± 17 | 11 | (73) |
| NANA | 26 | 9(34) | 24 ± 6 | 0 | (0) |
| +IFN | 30 | 5(16) | 39 ± 12 | 4 | (13) |
| +CP | 15 | 6(40) | 69 ± 12 | 8 | (53) |
| +CP +FN | 30 | 13(43) | 70 ± 12 | 11 | (36) |

Other sugars such as N-acetylglucosamine, glucoronate have comparable anti-tumour effects.

On the tenth day after grafting, the treatment with all the sugars tested, either alone or in association with corynebacterium parvum (CP) or IFN reduces considerably the incidence of the tumours. The mean survival is particularly increased by glucosamine and galacturonate. In the case of immunostimulation by CP alone, the total survival is considerably increased by glucosamine (53%) and lactose (43%). Association with IFN increases the mean survival, particularly in the case of lactose.

II—Study of the inhibiting effects of butyric amino acids with respect to SCLs

Indirect antitumour effects of butyric amino acids

The same experimental procedure was used as for the previous table, but using butyric salts: gamma aminobutyric (GABA), alpha aminobutyric, alpha-aminoiso-butyric and the reference medium.

The results obtained are summarised in Table 5.

TABLE 5

| Amino acid | No. of mice | Tumours on 10th day (%) | MST days | Number | Final survival (%) |
|---|---|---|---|---|---|
| GABA | 30 | 14(46) | 35 ± 9 | 4 | (13) |
| +IFN | 45 | 19(42) | 43 ± 10 | 11 | (24) |
| +CP | 45 | 25(55) | 68 ± 11 | 24 | (53) |
| +CP + IFN | 30 | 7(23) | 70 ± 13 | 17 | (56) |
| alphaaminobut. | 30 | 19(63) | 26 ± 1 | 0 | (0) |
| +IFN | 30 | 9(30) | 25 ± 2 | 0 | (0) |
| +CP | 30 | 18(60) | 55 ± 14 | 7 | (23) |
| CP + IFN | 30 | 7(23) | 62 ± 14 | 14 | (47) |
| alphaaminoiso. | 30 | 6(20) | 31 ± 7 | 2 | (7) |
| +IFN | 30 | 15(50) | 31 ± 10 | 4 | (13) |
| +CP | 30 | 14(46) | 66 ± 13 | 13 | (43) |
| CP + IFN | 30 | 12(4d) | 64 ± 13 | 14 | (47) |
| Medium | 105 | 94(89) | 19 ± 1 | 0 | (0) |
| +IFN | 105 | 65(68) | 25 ± 4 | 7 | (7) |
| +CP | 105 | 85(89) | 32 ± 5 | 10 | (10) |
| +CP + IFN | 105 | 43(41) | 60 ± 7 | 45 | (42) |

Under the same conditions as for the sugars that inhibit sarcolectin in the previous series, gamma aminobutyric acid and alpha aminoisobutyric acid inhibit oncogenesis significantly. The appearance of the tumours is retarded, the increase in the mean survival is obtained in all the groups. An injection of CP alone also brings about a significant increase in the final survival of the animals which is further increased in association with interferon.

As in the case of the inhibitory sugars, the SCLs of the invention are particularly valuable models for studying the anti-tumour effects of butyric amino acids and the development of a treatment protocol (Table 5).

III—Direct effects of sarcolectin on the stimulation of the synthesis of cell DNA The effect of sarcolectin on the synthesis of the DNA of various immunocompetent cells was verified: H9 T lymphocytes and Daudi B lymphocytes, U937 monocytes, and the following were studied in parallel: normal T and B lymphocytes originating from the spleen, murine L929 cells and human HeLa cells.

In all cases, the growth medium did not contain any serum, only highly purified sarcolectin as obtained according to example 1.

After 24 hours, the synthesis of the DNA of the various cell populations was analysed by comparing the reference cells treated with the same medium and without sarcolectin.

A significant increase in the synthesis of DNA is observed, particularly in the case of the H9, Daudi and U937 cells, a slightly lower increase for normal T and B lymphocytes and the HeLa cells, whereas it remained at the same high level as the non-anchored lines in the case of mice cells. These results clearly show that sarcolectin has its own stimulating effect on growth, which is independent of the more specific growth factors with which it is coupled.

In the biopsies taken during exeresis of osteogenic sarcomas in infants, the fragment secretes in the medium without serum considerable quantities of SCL identified by Western blotting tests using anti-55 kd antiserum.

Figure 5:
FIG. 5: the photo of a Western blot using the anti-55 kd antibody for studying various samples.

This same lectin is also detected in the ascitic fluid taken during the grafts of TG 180 sarcomas in mice (slope 4 in FIG. 5), slopes 1 to 3 corresponding to non-cancerous diseases, and slopes 5 to 8 corresponding to sera of human osteogenic sarcomas.

IV—Inhibiting effect of sarcolectin on the synthesis of secondary effector proteins of interferon The antagonistic effect of sarcolectin on the action of interferon may be assessed by treating the cells with interferon for 5 to 6 hours, then removing the medium and replacing it with sarcolectin for 18 hours. The antagonistic effect of SCL appears from the 5th hour onwards and may end in restoration of the cell to its initial state prior to the treatment with interferon. Sarcolectin is also able to inhibit the action of IFNs induced either by poly(I)(C) or by the Newcastle virus. These data suggest that, without affecting its production, the action of interferon (induced by poly(I) (C) may be inhibited by SCL, resulting in a reduction in or the complete disappearance of retro-inhibition.

Under these conditions, poly(I)(C)'s own effect on growth appears clearly. IFN and SCL are in equilibrium and also act on poly(I)(C) by modifying its expression; the whole process results in a triangular equilibrium.

V—Use of sarcolectin in diagnostics

As sarcolectin stimulates the synthesis of DNA and inhibits the secondary effector proteins of interferon, its presence may be tested for both in tumours and in various biological secretions, serum, ascitic fluids, placenta, etc.

Diagnostic techniques require a rapid method of purification.

The sarcolectin level in human or animal serum may be obtained, for example, in the following manner:

dilution of the serum to 1/10;

lowering the pH of the medium to pH 5 for 30 min at the temperature of the laboratory;

readjustment to pH 7.4; substantial precipitation is then observed, which must be removed by centrifugation at 10,000 rpm for 30 minutes;

readjustment of the pH of the supernatant obtained to pH 7.4.

The purified preparation contains only one band of 65 kd. However, in a high concentration, a band of 55 kd may be detected using western blotting with the aid of monoclonal antibodies or anti-sarcolectin monospecific antibodies.

VI—Detection of sarcolectin by agglutination of cells

By way of example, it is possible to use H9 cells originating from human T lymphomas, treated with 10% formaldehyde. The cells may be kept in a phosphate buffer without any special precautions. The concentration of the sarcolectin may be estimated by a range of geometric dilutions, generally base 2, in a microtitre plate to which is added a suspension of fixed cells. Agglutination occurs at 4° C. and the limit is estimated by the dilution at which about 50% of the cells are agglutinated.

VII—Analysis of sarcolectin by increasing the synthesis of cell DNA

The cell suspension to be tested must be incubated with the arbitrarily chosen quantity of tritiated thymidine. It is important that the medium does not contain any serum during the test period, which is generally 24 hours.

VIII—Use of SCLs in anti-tumour therapy

As described above, the use of SCL in anti-tumor therapy can be envisaged, on the condition that there is no prior constituent production of SCL.

This application is based on the analysis of the development of tissues whose growth is normal and rapid, such as the foetus. The placental blood contains on the one hand growth factors and SCLs which stimulate the synthesis of DNA, and on the other hand interferons which inhibit it by promoting cell differentiation.

These three types of factors appear in alternation, leading to discontinuous growth.

According to Lampl et al. (11), spurts of growth are short and abrupt lasting 24 hours, followed by 30 to 60-day rest periods.

On the basis of this information, the treatment proposed is as follows:

1. Sole stimulation of growth by the SCL administered parenterally in sufficient doses to increase the proliferation of leucocytes significantly in the blood. This function may be enhanced by aspartate salts (24 mM/kg) administered in parallel during the first 3 days. It may be replaced by cimetidine.

It is also possible to associate recombinant interleukin-2 under comparable conditions.

2. After a 4–5 day break, the treatment of targets includes IFNs, particularly of the α or β group injected every 48 hours parenterally (generally in doses of 3–5×$10^6$ units per injection) for one month. This treatment ensures better differentiation of the cells generated in phase 1. The effect of IFNs may be increased considerably by the butyric amino acids (5 g/kg) tested above.

3. The effect of interferons may be increased by association with the sugars mentioned above, particularly lactoses (α or β), D galactose, N-acetylneuraminic acid (N.A.N.A.) chosen for example, Their nature may vary in terms of the species or the tissues. For example, in osteogenic sarcomas in infants, the local treatment based on these concepts could usefully complement the surgical treatment, by associating SCL-aspartate, followed by IFN, α lactose, and N.A.N.A.

IX Reproduction of the essential biological functions with recombinant SCL

The cloned molecule was introduced into a plasmid containing 2 promoters, one of them being a promoter of inducible transcription by hexamethasone. The choice of this system is justified by the fact that SCL is in practice present in all of the cells studied to date and could be at the origin of the functions present in the host cell.

Mouse L cells were transfected with the plasmid containing the cloned gene. The anti-interferon function was studied by the capacity of interferon to inhibit the multiplication of a developer: the vesicular stomatitis virus. The interferon function was then quantified in the mouse cells (use of variable concentrations of interferon and investigation of the dilution limit at which the antiviral state is completely inhibited). The vesicular stomatitis virus destroys all of the cell population in the virgin cells.

The results obtained are set out in Table 6.

It is noted that in the presence of cells incubated with interferon for 5 hours, the antiviral function is expressed. From the fifth hour, the interferon is replaced by SCL for the following 18 hours, taking care to replace the SCL by the medium in the control cell; the recombinant SCL blocks the state of the antiviral effect while in the controls treated with the medium, the interferon already fixed on the receptors expresses all its functions normally.

In a second series of experiments, the susceptible cells were treated with 200 IU of interferon for 5 hours. Decreasing quantities of SCL, diluted according to a geometric scale to the base 2 were then added. In the example chosen, the 1/32 dilution was the limit at which the action of the interferon was completely blocked, viral multiplication is normally resumed.

TABLE 6

INHIBITION OF THE ACTION OF INTERFERON (IFN) BY RECOMBINANT SCL

| A. IFN TITER 32 U | |
|---|---|
| Control IFN. | 1280 U INT. REF. |
| IFN. + SCL. induced by hexamethasone | <2 U |
| IFN. + SCL. non-induced | >5120 U |
| B. SCL TITER* | |
| IFN. 200 U + medium | 1280 U |
| IFN. 200 U + SCL. | 32 U. 50%* |

*concentration of SCL which inhibits by 100% the antiviral state

Ix Induction of antibodies against the oligopeptides SEQ ID NO: 5 or SEQ ID NO: 6 .

By operating according to standard techniques, the formation of antibodies against the SEQ ID NO: 5 peptides or SEQ ID NO:6 is induced. The specific characters of these antibodies is set out in Table 7.

| Antiserum | Oligopeptide as Antigen | | |
|---|---|---|---|
| | 41–55 | 81–95 | Ost. Sarc. ESS |
| 41–55 | >12600 | <200 | >12800 |
| 81–95 | <200 | >12800 | ND |
| Anti-SCL monoclonal antibody | 4–800 | <200 | 6400 |

The antibodies induced by the SEQ ID NO: 5 peptides (oligopeptide 41–55 in SEQ ID NO: 1) and SEQ ID NO: 6 (oligopeptide 81–95 in SEQ ID NO: 1) respectively are specific for each of the peptides.

The SCLs excreted by the osteogenic sarcoma ESS are strongly recognised by the anti-peptide 41–55 antibodies.

XI Stimulation over 24 hours of the synthesis of DNA in T (lympho) cells

The SCL is excreted in the H-1 medium by PBMC over 24 hours maintained without serum. The results obtained are given in Table 8.

| IL2 (100 u) | EXP. N° 1 | EXP. N° 2 |
|---|---|---|
| +M | 4,081 ± 341 | 11,354 ± 772 |
| +SCL | 6,167 ± 483.66 | 35,438 ± 10.370 |
| +SCL + NANA (0.75 mmol.) | 4,657 ± 214.78 | 27,133 ± 1771 |
| +SCL + oligo 41–55 (3 µγ/ml) | 4,674 ± 832.52 | 23,184 ± 2494 |

SCL is the only protein detected with electrophoresis after staining with coomassie blue and identified by the monoclonal antibodies using Western Blot known as being of SCL.

Examination of the results in Table 8 show that SCL excreted from cells stimulates the synthesis of DNA over 24 hours.

This stimulation is inhibited by N.A.N.A. or by the oligopeptide 41–55 (SEQ ID NO: 5).

Bibliographical References

1/Fournier F., et al., (1969), Proc. Soc. Exp. Biol. Med. 132, 943
2/Chany C., et al, (1971), Nature, Biol. 230, 11
3/Fournier F. et al (1972) Nature New Biol., 274, 1757.
4/Chany, C. et al, (1969), C.R. Acad. Sci. Paris 269, 1236
5/Duc-Goiran P. et al. (1985), Proc. Nat. Acad. Sci USA, 82,5010
6/Chany C. et al (1969), 269,2628
7/Jiang P. H. et al (1988) Biol., Chemistry, 263, 19154
8/Chany-Fournier F. et al (1990). I of Cellular Physiology, 145, 173
9/Glass C. et al, (1985) J. Cell Biol. 101, 236
10/Sambrook J. et al, (1989) Cold Spring Harbor Laboratory Press
11/Lampl M et al, (1992) Science 258 ; 801
12/Fu-Yue Zeng et al, (1994) Bio Chem 375, 393–399.

---

What is claimed is:

1. An isolated peptide or protein having lectinic properties and comprising the amino acid sequence of SEQ ID NO:3.

2. An isolated peptide or protein having lectinic properties and comprising the amino acid sequence of SEQ ID NO:4.

3. An isolated peptide or protein having lectinic properties and comprising the amino acid sequence of SEQ ID NO:6.

4. An isolated peptide or protein, wherein the amino acid sequence of SEQ ID NO:3 comprises the amino acid sequence of the peptide or protein, wherein the peptide or protein has lectinic properties, and wherein the peptide or protein is recognized by an antibody specific to the peptide or protein of claim 1.

5. An isolated peptide or protein, wherein the amino acid sequence of SEQ ID NO:4 comprises the amino acid sequence of the peptide or protein, wherein the peptide or protein has lectinic properties, and wherein the peptide or protein is recognized by an antibody specific to the peptide or protein of claim 2.

6. An isolated peptide or protein, wherein the amino acid sequence of SEQ ID NO:6 comprises the amino acid sequence of the peptide or protein, wherein the peptide or protein has lectinic properties, and wherein the peptide or protein is recognized by an antibody specific to the peptide or protein of claim 3.

7. The peptide or protein of claim 1 obtained by a method comprising sequentially treating a tissue extract containing a lectin:
   (a) with pepsin or at an acidic pH to remove a majority of contaminating proteins while retaining lectinic activity,
   (b) by chromatography using SEPHACRYL S-200® (gel filtration media with a fractionation range of 5,000–250,000 daltons for globular proteins),
   (c) by chromatography using diethylaminoethyl cellulose,
   (d) by chromatography using CM-TRISACRYL-M® (gel filtration media with a fractionation range of 200–2,500 daltons),
   (e) by affinity chromatography using N-acetylneuraminic acid as a ligand, and
   (f) by reversed-phase high pressure liquid chromatography to separate the peptide or protein.

8. The peptide or protein of claim 7, wherein 55 kd and 14 kd bands are recovered if the peptide or protein is subjected to sodium dodecyl sulfate polyacrylamide gel electrophoresis.

9. A method for obtaining the peptide or protein of claim 1 comprising sequentially treating a tissue extract containing a lectin:
   (a) with pepsin or at an acidic pH to remove a majority of contaminating proteins while retaining lectinic activity,
   (b) by chromatography using SEPHACRYL S-200® (gel filtration media with a fractionation range of 5,000–250,000 daltons for globular proteins),
   (c) by chromatography using diethylaminoethyl cellulose,
   (d) by chromatography using CM-TRISACRYL-M® (gel filtration media with a fractionation range of 200–2,500 daltons), and
   (e) by affinity chromatography using N-acetylneuraminic acid as a ligand.

10. The method of claim 9, wherein (d) is conducted:
   (i) using a first buffer to remove the majority of contaminating albumin, and
   (ii) using a second buffer to elute the lectin.

11. The method of claim 9, wherein the ligand is attached to an agarose gel column, and (e) is conducted:
   (i) using a first buffer to elute the lectin, and
   (ii) using a second buffer to remove the majority of contaminating proteins.

12. The method of claim 9, comprising, after (e), treating the extract by high pressure liquid chromatography.

13. The method of claim 12, wherein the high pressure liquid chromatography is conducted using water/acetonitrile/trifluoroacetic acid.

14. The method of claim 13, wherein 65 kd, 55 kd, and 14 kd bands are recovered if a fraction corresponding to the main peak obtained during the high pressure liquid chromatography is subjected to sodium dodecyl sulfate polyacrylamide gel electrophoresis.

15. A growth factor useful for contributing to regeneration of damaged tissues and to improving the wound healing process, comprising the peptide of claim 1.

16. A growth factor useful for contributing to regeneration of damaged tissues and to improving the wound healing process, comprising the peptide of claim 2.

17. A growth factor useful for contributing to regeneration of damaged tissues and to improving the wound healing process, comprising the peptide of claim 3.

18. A growth factor useful for contributing to regeneration of damaged tissues and to improving the wound healing process, comprising the peptide of claim 4.

19. A growth factor useful for contributing to regeneration of damaged tissues and to improving the wound healing process, comprising the peptide of claim 5.

20. A growth factor useful for contributing to regeneration of damaged tissues and to improving the wound healing process, comprising the peptide of claim 6.

21. A therapeutic agent for stimulating the immune system comprising the peptide of claim 1.

22. The therapeutic agent of claim 21, further comprising interleukin-2.

23. A therapeutic agent for stimulating the immune system comprising the peptide of claim 2.

24. The therapeutic agent of claim 23, further comprising interleukin-2.

25. A therapeutic agent for stimulating the immune system comprising (i) an isolated peptide or protein having lectinic properties and comprising the amino acid sequence of SEO ID NO:5, (ii) interleukin-2, and (iii) a pharmaceutical excipient.

26. A therapeutic agent for stimulating the immune system comprising the peptide of claim 3.

27. The therapeutic agent of claim 26, further comprising interleukin-2.

28. A therapeutic agent for stimulating the immune system comprising an isolated peptide or protein, wherein the amino acid sequence of SEQ ID NO:3 comprises the amino acid sequence of the peptide or protein, wherein the peptide or protein has lectinic properties, and wherein the peptide or protein is recognized by an antibody specific to an isolated peptide or protein having lectinic properties and comprising the amino acid sequence of SEQ ID NO:3.

29. The therapeutic agent of claim 28, further comprising interleukin-2.

30. A therapeutic agent for stimulating the immune system comprising the peptide of claim 5.

31. The therapeutic agent of claim 30, further comprising interleukin-2.

32. A therapeutic agent for stimulating the immune system comprising an isolated peptide or protein, wherein the amino acid sequence of SEQ ID NO:5 comprises the amino acid sequence of the peptide or protein, wherein the peptide or protein has lectinic properties, and wherein the peptide or protein is recognized by an antibody specific to an isolated peptide or protein having lectinic properties and comprising the amino acid sequence of SEQ ID NO:5, and further comprising interleukin-2.

33. A therapeutic agent for stimulating the immune system comprising the peptide of claim 4.

34. The therapeutic agent of claim 33, further comprising interleukin-2.

35. A therapeutic agent for stimulating the immune system comprising an isolated peptide or protein having lectinic properties and comprising the amino acid sequence of SEQ ID NO:3, in monomer or dimer form.

36. A therapeutic agent for stimulating the immune system comprising an isolated peptide or protein having lectinic properties and comprising the amino acid sequence of SEQ ID NO:4, in monomer or dimer form.

37. A therapeutic agent for stimulating the immune system comprising an isolated peptide or protein having lectinic properties and comprising the amino acid sequence of SEQ ID NO:6, in monomer or dimer form.

38. A method of stimulating the immune system, comprising administering, to a subject in need of such stimulation, an isolated peptide or protein having lectinic properties and comprising the amino acid sequence of SEQ ID NO:3, and a pharmaceutical excipient.

39. A method of stimulating the immune system, comprising administering, to a subject in need of such stimulation, an isolated peptide or protein having lectinic properties and comprising the amino acid sequence of SEQ ID NO:4, and a pharmaceutical excipient.

40. A method of stimulating the immune system, comprising administering, to a subject in need of such stimulation, an isolated peptide or protein having lectinic properties and comprising the amino acid sequence of SEQ ID NO:6, and a pharmaecutical excipient.

41. A therapeutic agent as claimed in claim 21, additionally comprising a pharmaceutical excipient.

42. A therapeutic agent as claimed in claim 23, additionally comprising a pharmaceutical excipient.

43. A therapeutic agent as claimed in claim 26, additionally comprising a pharmaceutical excipient.

44. A therapeutic agent according to claim 41, formulated for parenteral administration.

45. A therapeutic agent according to claim 42, formulated for parenteral administration.

46. A therapeutic agent according to claim 43, formulated for parenteral administration.

\* \* \* \* \*